US009814782B2

(12) United States Patent
Park et al.

(10) Patent No.: US 9,814,782 B2
(45) Date of Patent: *Nov. 14, 2017

(54) MODIFIED ANTIBODY IN WHICH MOTIF COMPRISING CYSTEINE RESIDUE IS BOUND, MODIFIED ANTIBODY-DRUG CONJUGATE COMPRISING THE MODIFIED ANTIBODY, AND PRODUCTION METHOD FOR SAME

(71) Applicant: Alteogen Inc., Daejeon (KR)

(72) Inventors: Soon Jae Park, Daejeon (KR);
Hye-Shin Chung, Daejeon (KR);
Seonhun Kwon, Seoul (KR); Sunbae Lee, Daejeon (KR); Sun-ah Yoo, Daejeon (KR); Yong Mo Kim, Jeoneup-si (KR)

(73) Assignee: ALTEOGEN INC., Daejeon (KR)

(*) Notice: Subject to any disclaimer, the term of this patent is extended or adjusted under 35 U.S.C. 154(b) by 0 days.

This patent is subject to a terminal disclaimer.

(21) Appl. No.: 14/380,068

(22) PCT Filed: Feb. 22, 2013

(86) PCT No.: PCT/KR2013/001417
§ 371 (c)(1),
(2) Date: Aug. 20, 2014

(87) PCT Pub. No.: WO2013/125891
PCT Pub. Date: Aug. 29, 2013

(65) Prior Publication Data
US 2016/0102148 A1 Apr. 14, 2016

(30) Foreign Application Priority Data

Feb. 24, 2012 (KR) ........................ 10-2012-0019221

(51) Int. Cl.
*A61K 47/68* (2017.01)
*A61K 47/65* (2017.01)
*C07K 16/00* (2006.01)
*C07K 16/30* (2006.01)
*C07K 16/32* (2006.01)
*A61K 31/704* (2006.01)
*A61K 38/07* (2006.01)
*A61K 38/08* (2006.01)
*A61K 47/48* (2006.01)

(52) U.S. Cl.
CPC ...... *A61K 47/48584* (2013.01); *A61K 31/704* (2013.01); *A61K 38/07* (2013.01); *A61K 47/65* (2017.08); *A61K 47/6803* (2017.08); *A61K 47/6809* (2017.08); *A61K 47/6817* (2017.08); *A61K 47/6849* (2017.08); *A61K 47/6851* (2017.08); *A61K 47/6855* (2017.08); *A61K 47/6871* (2017.08); *C07K 16/00* (2013.01); *C07K 16/30* (2013.01); *C07K 16/3015* (2013.01); *C07K 16/32* (2013.01); *C07K 2317/24* (2013.01); *C07K 2317/52* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,821,337 A | * | 10/1998 | Carter .................... C07K 16/28 424/133.1 |
| 6,214,345 B1 | | 4/2001 | Firestone et al. |
| 7,723,485 B2 | | 5/2010 | Junutula et al. |
| 7,745,394 B2 | | 6/2010 | Doronina et al. |
| 2004/0018194 A1 | | 1/2004 | Franscisco et al. |
| 2007/0092940 A1 | * | 4/2007 | Eigenbrot ........ A61K 47/48538 435/69.1 |

(Continued)

FOREIGN PATENT DOCUMENTS

| | | |
|---|---|---|
| EA | 010970 B1 | 12/2008 |
| EA | 011882 B1 | 6/2009 |

(Continued)

OTHER PUBLICATIONS

Argos, P. (J. Mol. Biol. 1990 211, 943-958).*
Penichet, M., et al., "Design and Engineering Human Forms of Monoclonal Antibodies", Drug Development Research, Jul. 19, 2004, pp. 121-136, vol. 61.
Rogers, J., et al., "Rapid discovery and optimization of therapeutic antibodies against emerging infectious diseases", Protein Engineering, Design & Selection, May 13, 2008, pp. 495-505, vol. 21, No. 8.
Allen, S., et al., "Cu(I) affinities of the domain 1 and 3 sites in the human metallochaperone for Cu,Zn-superoxide dismutase", "Biochemistry", Feb. 9, 2012, pp. 1439-1448, vol. 51, No. 7.

(Continued)

*Primary Examiner* — Peter J Reddig
(74) *Attorney, Agent, or Firm* — Hultquist, PLLC; Steven J. Hultquist

(57) ABSTRACT

The present invention relates to an antibody in which a motif composed of an amino acid or peptide sequence including one or more cysteine residues is bound to the terminus of a parent antibody, particularly the terminus of the heavy chain of the parent antibody. Also, the present invention relates to a modified antibody-drug conjugate (mADC) comprising a drug bound to the antibody, and a method for producing the antibody or the modified antibody-drug conjugate. The modified antibody-drug conjugate according to the invention can accurately deliver the drug to a target cell due its high specificity to antigen, and thus can increase the therapeutic effect of the drug. Also, it can increase the usability of drugs, particularly anticancer drugs, the use of which is restricted due to their toxicity, despite their high efficacy. Moreover, the invention relates to a composition for treatment of diseases, particularly cancers, which comprise the modified antibody-drug conjugate.

16 Claims, 6 Drawing Sheets

(56) References Cited

U.S. PATENT DOCUMENTS

| | | |
|---|---|---|
| 2009/0202536 A1 | 8/2009 | Ebens et al. |
| 2010/0143368 A1* | 6/2010 | King ............... A61K 47/48561 424/142.1 |
| 2011/0280891 A1* | 11/2011 | Liu ................. A61K 47/48384 424/181.1 |
| 2017/0119903 A1* | 5/2017 | Park ................ A61K 47/48584 |

FOREIGN PATENT DOCUMENTS

| | | | |
|---|---|---|---|
| EP | 1391213 A1 | 2/2004 | |
| KR | 1020070054682 A | 5/2007 | |
| KR | 100766952 B1 | 10/2007 | |
| KR | 1020100090267 A | 8/2010 | |
| RU | 2404810 C2 | 11/2010 | |
| WO | WO 94/26295 * | 11/1994 | ............... C07K 5/00 |
| WO | 9600087 A2 | 1/1996 | |
| WO | 03031475 A2 | 4/2003 | |
| WO | 2004032828 A2 | 4/2004 | |
| WO | 2004053130 A1 | 6/2004 | |
| WO | 2005117986 A2 | 12/2005 | |
| WO | 2006034488 A2 | 3/2006 | |
| WO | 2006082517 A1 | 8/2006 | |
| WO | 2007140371 A2 | 12/2007 | |
| WO | 2008140538 A1 | 11/2008 | |
| WO | 2009026274 A1 | 2/2009 | |
| WO | 2009052249 A1 | 4/2009 | |
| WO | 2011054519 A1 | 5/2011 | |
| WO | 2011156328 A1 | 12/2011 | |

OTHER PUBLICATIONS

Ansbacher, T., et al., "Predicting the coordination number within copper chaperones: Atox1 as case study", "J. Phys. Chem. B", Apr. 5, 2012, pp. 4425-4432, vol. 116, No. 15.

Basle, E., et al., "Protein chemical modification on endogenous amino acids", "Chem. Biol.", Mar. 26, 2010, pp. 213-227, vol. 17, No. 3.

Bayascas, J., et al., "Isolation of AmphiCASP-3/7, an ancestral caspase from amphioxus (Branchiostoma floridae). Evolutionary considerations for vertebrate caspases", "Cell Death Differ.", Oct. 2002, pp. 1078-1089, vol. 9, No. 10.

Bhaskar, V., et al., "E-selectin up-regulation allows for targeted drug delivery in prostate cancer", "Cancer Res.", Oct. 1, 2003, pp. 6387-6394, vol. 63, No. 19.

Burris, H., et al., "Phase II study of the antibody drug conjugate trastuzumab-DM1 for the treatment of human epidermal growth factor receptor 2 (HER2)-positive breast cancer after prior HER2-directed therapy", "J. Clin. Oncol.", Dec. 20, 2010, pp. 398-405, vol. 29, No. 4.

Click, T., et al., "Importance of electrostatic polarizability in calculating cysteine acidity constants and copper(I) binding energy of Bacillus subtilis CopZ", "J. Comput. Chem.", Feb. 27, 2012, pp. 1142-1151, vol. 33, No. 11.

Cochran, J., et al., "A metal switch for controlling the activity of molecular motor proteins", "Nat. Struct. Mol. Biol.", Dec. 25, 2011, pp. 122-127, vol. 19, No. 1.

Doronina, S., et al., "Development of potent monoclonal antibody auristatin conjugates for cancer therapy", "Nat. Biotechnol.", Jun. 1, 2003, pp. 778-784, vol. 21, No. 7.

Draper, J., et al., "Identification of a chemoreceptor zinc-binding domain common to cytoplasmic bacterial chemoreceptors", "J. Bacteriol.", Jul. 1, 2011, pp. 4338-4345, vol. 193, No. 17.

Francisco, J., et al., "cAC10-vcMMAE, an anti-CD30-monomethyl auristatin E conjugate with potent and selective antitumor activity", "Blood", Apr. 24, 2003, pp. 1458-1465, vol. 102, No. 4.

Guenther, V., et al., "A conserved cysteine cluster, essential for transcriptional activity, mediates homodimerization of human metal-responsive transcription factor-1 (MTF-1)", "Biochim. Biophys. Acta", Oct. 25, 2011, pp. 476-483, vol. 1823, No. 2.

Hall, J., et al., "Transition metal transporters in plants", "Journal of Experimental Botany", Oct. 29, 2003 , pp. 2601-2613, vol. 54, No. 393.

Hamblett, K., et al., "Effects of drug loading on the antitumor activity of a monoclonal antibody drug conjugate", "Clin. Cancer Res.", Oct. 15, 2004, pp. 7063-7070, vol. 10, No. 20.

Hanikenne, M., et al., "A comparative inventory of metal transporters in the green alga Chlamydomonas reinhardtii and the red alga Cyanidioschizon merolae", "Plant Physiol.", Feb. 2005, pp. 428-446, vol. 137, No. 2.

Hinman, L., et al., "Preparation and characterization of monoclonal antibody conjugates of the calicheamicins: a novel and potent family of antitumor antibiotics", "Cancer Res.", Jul. 15, 1993, pp. 3336-3342, vol. 53, No. 14.

Isakoff, S., et al., "Trastuzumab-DM1: building a chemotherapy-free road in the treatment of human epidermal growth factor receptor 2-positive breast cancer", "J. Clin. Oncol.", Dec. 20, 2010, pp. 351-354, vol. 29, No. 4.

Jancso, A., et al., "Towards the role of metal ions in the structural variability of proteins: CdII speciation of a metal ion binding loop motif", "Metallomics", Oct. 31, 2011, pp. 1331-1339, vol. 3, No. 12.

Junutula, J., et al., "Site-specific conjugation of a cytotoxic drug to an antibody improves the therapeutic index", "Nat. Biotechnol.", Jul. 20, 2008, pp. 925-932, vol. 26, No. 8.

Klussman, K., et al., "Secondary mAb-vcMMAE conjugates are highly sensitive reporters of antibody internalization via the lysosome pathway", "Bioconjugate Chem.", Jul.-Aug. 2004, pp. 765-773, vol. 15, No. 4.

Liu, C., et al., "Eradication of large colon tumor xenografts by targeted delivery of maytansinoids", "Proc. Natl. Acad. Sci. USA", Aug. 6, 1996, pp. 8618-8623, vol. 93.

Lode, H., et al., "Targeted therapy with a novel enediyene antibiotic calicheamicin theta(I)1 effectively suppresses growth and dissemination of liver metastases in a syngeneic model of murine neuroblastoma", "Cancer Res.", Jul. 15, 1998, pp. 2925-2928, vol. 58, No. 14.

MacPherson(2006), "A Fungal Family of Transcriptional Regulators: the Zinc Cluster Proteins", "Microbiol. Mol. Biol. Rev.", Sep. 2006, pp. 583-604, vol. 70, No. 3.

Mandler, R., et al., "Immunoconjugates of geldanamycin and anti-HER2 monoclonal antibodies: antiproliferative activity on human breast carcinoma cell lines", "J. Natl. Cancer Inst.", Oct. 4, 2000, pp. 1573-1581, vol. 92, No. 19.

Mandler, R., et al., "Synthesis and evaluation of antiproliferative activity of a geldanamycin-Herceptin immunoconjugate", "Bioorganic & Medicinal Chemistry Letters", May 15, 2000, pp. 1025-1028, vol. 10, No. 10.

Mandler, R., et al., "Modifications in synthesis strategy improve the yield and efficacy of geldanamycin-herceptin immunoconjugates", "Bioconjugate Chem.", Jul.-Aug. 2002, pp. 786-791, vol. 13, No. 4.

Mao, W., et al., "EphB2 as a therapeutic antibody drug target for the treatment of colorectal cancer", "Cancer Res.", Feb. 1, 2004, pp. 781-788, vol. 64, No. 3.

Nivorozhkin, A., et al., "Metallocyclopeptide complexes with MII(S.Cys)4 chromophores", "Inorg. Chem.", May 290, 2000, pp. 2306-2313, vol. 39, No. 11.

Peackock, A., et al., "Harnessing natures ability to control metal ion coordination geometry using de novo designed peptides", "Dalton Trans.", Jan. 16, 2009, pp. 2271-2280, vol. 13.

Phillips, G., et al., "Targeting HER2-positive breast cancer with trastuzumab-DM1, an antibody-cytotoxic drug conjugate", "Cancer Res.", Nov. 15, 2008, pp. 9280-9290, vol. 68, No. 22.

Preaudat, M., et al., "A homogeneous caspase-3 activity assay using HTRF technology", "J. Biomol. Screen.", Jun. 2002, pp. 267-274, vol. 7, No. 3.

Rabasseda, X., et al., "Gemtuzumab ozogamicin. Treatment of acute myeloid leukemia", "Drugs of the Future", Jul. 2000, pp. 686-692, vol. 25, No. 7.

Roehm, P., et al., "Selectivity of Methylation of Metal-Bound Cysteinates and Its Consequences", "J. Am. Chem. Soc.", Dec. 4, 1998, pp. 13083-13087, vol. 120, No. 50.

Schaeffer, D., et al., "The CR3 motif of Rrp44p is important for interaction with the core exosome and exosome function", "Nucleic Acids Res.", Jul. 24, 2012, pp. 9298-9307, vol. 40, No. 18.

(56) References Cited

OTHER PUBLICATIONS

Singh, R., et al., "Labeling of antibodies by in situ modification of thiol groups generated from selenol-catalyzed reduction of native disulfide bonds", "Anal. Biochem.", May 15, 2002, pp. 147-156, vol. 304, No. 2.

Sitthisak, S., et al., "McsA and the roles of metal-binding motif in *Staphylococcus aureus*", "FEMS Microbiol. Lett.", Dec. 20, 2011, pp. 126-133, vol. 327, No. 2.

Van Horn, J., et al., "The Cys-Xaa-His metal-binding motif: [N] versus [S] coordination and nickel-mediated formation of cysteinyl sulfinic acid", "J. Biol. Inorg. Chem.", Jun. 21, 2003, pp. 601-610, vol. 8, No. 6.

Wang, L., et al., "Structural characterization of the maytansinoid-monoclonal antibody immunoconjugate, huN901-DM1, by mass spectrometry", "Protein Sci.", Aug. 4, 2005, pp. 2436-2446, vol. 14, No. 9.

Witzig, T., et al., "Treatment With Ibritumomab Tiuxetan Radioimmunotherapy in Patients With Rituximab-Refractory Follicular Non-Hodgkin's Lymphoma", "J. Clin Oncol.", Aug. 1, 2002, pp. 3262-3269, vol. 20, No. 15.

Xie, H., et al., "Pharmacokinetics and biodistribution of the anti-tumor immunoconjugate, cantuzumab mertansine (huC242-DM1), and its two components in mice", "J. Pharmacol. Exp. Ther.", Nov. 21, 2003, pp. 1073-1082, vol. 308, No. 3.

Zhang, L., et al., "Isolation of metallothionein genes and in silico structural characterization of their proteins using molecular modeling from yak (*Bos grunniens*)", "Biochem. Genet.", Mar. 8, 2012, pp. 585-599, vol. 50, No. 7-8.

Zhou, L., et al., "Cu(I)- and proton-binding properties of the first N-terminal soluble domain of Bacillus subtilis CopA", "FEBS J.", Dec. 6, 2011, pp. 285-298, vol. 279, No. 2.

Zielazinski, E., et al., "Characterization of a Cobalt-Specific P1B-ATPase", "Biochemistry", Sep. 25, 2012, pp. 7891-7900, vol. 51, No. 40.

* cited by examiner (A)

(B)

```
                          SEQUENCE LISTING

<160> NUMBER OF SEQ ID NOS: 128

<210> SEQ ID NO 1
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 1

Tyr Lys Cys Lys Gln Cys Gly Lys Ala Phe Gly Cys Pro Ser Asn Leu
1               5                   10                  15

Arg Arg His Gly Arg Thr His
            20

<210> SEQ ID NO 2
<211> LENGTH: 24
<212> TYPE: PRT
<213> ORGANISM: Artificial Sequence
<220> FEATURE:
<223> OTHER INFORMATION: metal ion binding motif of zinc finger protein

<400> SEQUENCE: 2

Tyr Gln Cys Asn Ile Cys Gly Gly Lys Cys Phe Ser Cys Asn Ser Asn
1               5                   10                  15

Leu His Arg His Gln Arg Thr His
            20

<210> SEQ ID NO 3
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 3

Tyr Ser Cys Gly Ile Cys Gly Lys Ser Phe Ser Asp Ser Ser Ala Lys
1               5                   10                  15

Arg Arg His Cys Ile Leu His
            20

<210> SEQ ID NO 4
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 4

Tyr Thr Cys Ser Asp Cys Gly Lys Ala Phe Arg Asp Lys Ser Cys Leu
1               5                   10                  15

Asn Arg His Arg Arg Thr His
            20

<210> SEQ ID NO 5
<211> LENGTH: 24
```

-continued

```
<212> TYPE: PRT
<213> ORGANISM: Artificial Sequence
<220> FEATURE:
<223> OTHER INFORMATION: metal ion binding motif of zinc finger protein

<400> SEQUENCE: 5

Tyr Arg Cys Lys Tyr Cys Asp Arg Ser Phe Ser Asp Ser Ser Asn Leu
1               5                   10                  15

Gln Arg His Val Arg Asn Ile His
            20

<210> SEQ ID NO 6
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 6

Tyr Lys Cys Lys Glu Cys Gly Lys Ala Phe Asn His Ser Ser Asn Phe
1               5                   10                  15

Asn Lys His His Arg Ile His
            20

<210> SEQ ID NO 7
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 7

Phe Lys Cys Pro Val Cys Gly Lys Ala Phe Arg His Ser Ser Ser Leu
1               5                   10                  15

Val Arg His Gln Arg Thr His
            20

<210> SEQ ID NO 8
<211> LENGTH: 25
<212> TYPE: PRT
<213> ORGANISM: Artificial Sequence
<220> FEATURE:
<223> OTHER INFORMATION: metal ion binding motif of zinc finger protein

<400> SEQUENCE: 8

Tyr Arg Cys Lys Tyr Cys Cys Asp Arg Ser Phe Ser Ile Ser Ser Asn
1               5                   10                  15

Leu Gln Arg His Val Arg Asn Ile His
            20                  25

<210> SEQ ID NO 9
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 9

Tyr Glu Cys Asp His Cys Gly Lys Ala Phe Ser Ile Gly Ser Asn Leu
1               5                   10                  15

Asn Val His Arg Arg Ile His
            20

<210> SEQ ID NO 10
```

```
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 10

Tyr Gly Cys His Leu Cys Cys Lys Ala Phe Ser Lys Ser Ser Asn Leu
1               5                   10                  15

Arg Arg His Glu Met Ile His
            20

<210> SEQ ID NO 11
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 11

Tyr Lys Cys Lys Glu Cys Gly Gln Ala Phe Arg Gln Arg Ala His Leu
1               5                   10                  15

Ile Arg His His Lys Leu His
            20

<210> SEQ ID NO 12
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 12

Tyr Lys Cys His Gln Cys Gly Lys Ala Phe Ile Gln Ser Phe Asn Leu
1               5                   10                  15

Arg Arg His Glu Arg Thr His
            20

<210> SEQ ID NO 13
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 13

Phe Gln Cys Asn Gln Cys Gly Ala Ser Phe Thr Gln Lys Gly Asn Leu
1               5                   10                  15

Asn Arg His Ile Lys Leu His
            20

<210> SEQ ID NO 14
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 14

Tyr Thr Cys Ser Tyr Cys Gly Lys Ser Phe Thr Gln Ser Asn Thr Leu
1               5                   10                  15

Lys Gln His Thr Arg Ile His
            20
```

```
<210> SEQ ID NO 15
<211> LENGTH: 22
<212> TYPE: PRT
<213> ORGANISM: Artificial Sequence
<220> FEATURE:
<223> OTHER INFORMATION: metal ion binding motif of zinc finger protein

<400> SEQUENCE: 15

Tyr Ala Cys His Leu Cys Gly Lys Ala Phe Thr Gln Ser Ser His Arg
1               5                   10                  15

Arg His Glu Lys Thr His
            20

<210> SEQ ID NO 16
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 16

Tyr Lys Cys Gly Gln Cys Gly Lys Phe Tyr Ser Gln Val Ser His Leu
1               5                   10                  15

Thr Arg His Gln Lys Ile His
            20

<210> SEQ ID NO 17
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 17

Tyr Ala Cys His Leu Cys Gly Lys Ala Phe Thr Gln Cys Ser His Leu
1               5                   10                  15

Arg Arg His Glu Lys Thr His
            20

<210> SEQ ID NO 18
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 18

Tyr Ala Cys His Leu Cys Ala Lys Ala Phe Ile Gln Cys Ser His Leu
1               5                   10                  15

Arg Arg His Glu Lys Thr His
            20

<210> SEQ ID NO 19
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 19

Tyr Val Cys Arg Glu Cys Gly Arg Gly Phe Arg Gln His Ser His Leu
1               5                   10                  15

Val Arg His Lys Arg Thr His
            20
```

```
<210> SEQ ID NO 20
<211> LENGTH: 24
<212> TYPE: PRT
<213> ORGANISM: Artificial Sequence
<220> FEATURE:
<223> OTHER INFORMATION: metal ion binding motif of zinc finger protein

<400> SEQUENCE: 20

Tyr Lys Cys Glu Glu Cys Glu Gly Lys Ala Phe Arg Gln Ser Ser His
1               5                   10                  15

Leu Thr Thr His Lys Ile Ile His
            20

<210> SEQ ID NO 21
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 21

Tyr Glu Cys Asp His Cys Gly Lys Ser Phe Ser Gln Ser Ser His Leu
1               5                   10                  15

Asn Val His Lys Arg Thr His
            20

<210> SEQ ID NO 22
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 22

Tyr Met Cys Ser Glu Cys Gly Arg Gly Phe Ser Gln Lys Ser Asn Leu
1               5                   10                  15

Thr Ile His Gln Arg Thr His
            20

<210> SEQ ID NO 23
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 23

Tyr Lys Cys Glu Glu Cys Gly Lys Ala Phe Thr Gln Ser Ser Asn Leu
1               5                   10                  15

Thr Lys His Lys Lys Ile His
            20

<210> SEQ ID NO 24
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 24

Phe Glu Cys Lys Asp Cys Gly Lys Ala Phe Ile Gln Lys Ser Asn Leu
1               5                   10                  15

Ile Arg His Gln Arg Thr His
            20
```

```
<210> SEQ ID NO 25
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 25

Tyr Val Cys Arg Glu Cys Arg Arg Gly Phe Ser Gln Lys Ser Asn Leu
1               5                   10                  15

Ile Arg His Gln Arg Thr His
            20

<210> SEQ ID NO 26
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 26

Tyr Glu Cys Glu Lys Cys Gly Lys Ala Phe Asn Gln Ser Ser Asn Leu
1               5                   10                  15

Thr Arg His Lys Lys Ser His
            20

<210> SEQ ID NO 27
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 27

Tyr Glu Cys Val Gln Cys Gly Lys Ser Tyr Ser Gln Ser Ser Asn Leu
1               5                   10                  15

Phe Arg His Gln Arg Arg His
            20

<210> SEQ ID NO 28
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 28

Tyr Glu Cys Val Gln Cys Gly Lys Gly Phe Thr Gln Ser Ser Asn Leu
1               5                   10                  15

Ile Thr His Gln Arg Val His
            20

<210> SEQ ID NO 29
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 29

Tyr Glu Cys Asn Thr Cys Arg Lys Thr Phe Ser Gln Lys Ser Asn Leu
1               5                   10                  15

Ile Val His Gln Arg Thr His
```

<210> SEQ ID NO 30
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 30

Tyr Val Cys Ser Lys Cys Gly Lys Ala Phe Thr Gln Ser Ser Asn Leu
1               5                   10                  15

Thr Val His Gln Lys Ile His
            20

<210> SEQ ID NO 31
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 31

Tyr Lys Cys Asp Glu Cys Gly Lys Asn Phe Thr Gln Ser Ser Asn Leu
1               5                   10                  15

Ile Val His Lys Arg Ile His
            20

<210> SEQ ID NO 32
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 32

Tyr Glu Cys Asp Val Cys Gly Lys Thr Phe Thr Gln Lys Ser Asn Leu
1               5                   10                  15

Gly Val His Gln Arg Thr His
            20

<210> SEQ ID NO 33
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 33

Tyr Lys Cys Pro Asp Cys Gly Lys Ser Phe Ser Gln Ser Ser Ser Leu
1               5                   10                  15

Ile Arg His Gln Arg Thr His
            20

<210> SEQ ID NO 34
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 34

Tyr Glu Cys Gln Asp Cys Gly Arg Ala Phe Asn Gln Asn Ser Ser Leu
1               5                   10                  15

```
<210> SEQ ID NO 35
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 35

Tyr Glu Cys Asn Glu Cys Gly Lys Phe Phe Ser Gln Ser Ser Ser Leu
1               5                   10                  15

Ile Arg His Arg Arg Ser His
            20

<210> SEQ ID NO 36
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 36

Tyr Lys Cys Glu Glu Cys Gly Lys Ala Phe Asn Gln Ser Ser Thr Leu
1               5                   10                  15

Thr Arg His Lys Ile Val His
            20

<210> SEQ ID NO 37
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 37

Tyr Glu Cys Asn Glu Cys Gly Lys Ala Phe Ala Gln Asn Ser Thr Leu
1               5                   10                  15

Arg Val His Gln Arg Ile His
            20

<210> SEQ ID NO 38
<211> LENGTH: 24
<212> TYPE: PRT
<213> ORGANISM: Artificial Sequence
<220> FEATURE:
<223> OTHER INFORMATION: metal ion binding motif of zinc finger protein

<400> SEQUENCE: 38

Tyr Glu Val His Asp Cys Gly Lys Ser Phe Arg Gln Ser Thr His Thr
1               5                   10                  15

Leu Thr Gln His Arg Arg Ile His
            20

<210> SEQ ID NO 39
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 39

Tyr Glu Cys His Asp Cys Gly Lys Ser Phe Arg Gln Ser Thr His Leu
1               5                   10                  15
```

Thr Arg His Arg Arg Ile His
            20

<210> SEQ ID NO 40
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 40

His Lys Cys Leu Glu Cys Gly Lys Cys Phe Ser Gln Asn Thr His Leu
1               5                   10                  15

Thr Arg His Gln Arg Thr His
            20

<210> SEQ ID NO 41
<211> LENGTH: 25
<212> TYPE: PRT
<213> ORGANISM: Artificial Sequence
<220> FEATURE:
<223> OTHER INFORMATION: metal ion binding motif of zinc finger protein

<400> SEQUENCE: 41

Tyr Val Cys Asp Val Glu Gly Cys Thr Trp Lys Phe Ala Arg Ser Asp
1               5                   10                  15

Glu Leu Asn Arg His Lys Lys Arg His
            20                  25

<210> SEQ ID NO 42
<211> LENGTH: 25
<212> TYPE: PRT
<213> ORGANISM: Artificial Sequence
<220> FEATURE:
<223> OTHER INFORMATION: metal ion binding motif of zinc finger protein

<400> SEQUENCE: 42

Tyr His Cys Asp Trp Asp Gly Cys Gly Trp Lys Phe Ala Arg Ser Asp
1               5                   10                  15

Glu Leu Thr Arg His Tyr Arg Lys His
            20                  25

<210> SEQ ID NO 43
<211> LENGTH: 25
<212> TYPE: PRT
<213> ORGANISM: Artificial Sequence
<220> FEATURE:
<223> OTHER INFORMATION: metal ion binding motif of zinc finger protein

<400> SEQUENCE: 43

Tyr Arg Cys Ser Trp Glu Gly Cys Glu Trp Arg Phe Ala Arg Ser Asp
1               5                   10                  15

Glu Leu Thr Arg His Phe Arg Lys His
            20                  25

<210> SEQ ID NO 44
<211> LENGTH: 25
<212> TYPE: PRT
<213> ORGANISM: Artificial Sequence
<220> FEATURE:
<223> OTHER INFORMATION: metal ion binding motif of zinc finger protein

<400> SEQUENCE: 44

Phe Ser Cys Ser Trp Lys Gly Cys Glu Arg Arg Phe Ala Arg Ser Asp

```
1               5                   10                  15
Glu Leu Ser Arg His Arg Arg Thr His
            20                  25

<210> SEQ ID NO 45
<211> LENGTH: 25
<212> TYPE: PRT
<213> ORGANISM: Artificial Sequence
<220> FEATURE:
<223> OTHER INFORMATION: metal ion binding motif of zinc finger protein

<400> SEQUENCE: 45

Phe Ala Cys Ser Trp Gln Asp Cys Asn Lys Lys Phe Ala Arg Ser Asp
1               5                   10                  15
Glu Leu Ala Arg His Tyr Arg Thr His
            20                  25

<210> SEQ ID NO 46
<211> LENGTH: 25
<212> TYPE: PRT
<213> ORGANISM: Artificial Sequence
<220> FEATURE:
<223> OTHER INFORMATION: metal ion binding motif of zinc finger protein

<400> SEQUENCE: 46

Tyr His Cys Asn Trp Asp Gly Cys Gly Trp Lys Phe Ala Arg Ser Asp
1               5                   10                  15
Glu Leu Thr Arg His Tyr Arg Lys His
            20                  25

<210> SEQ ID NO 47
<211> LENGTH: 24
<212> TYPE: PRT
<213> ORGANISM: Artificial Sequence
<220> FEATURE:
<223> OTHER INFORMATION: metal ion binding motif of zinc finger protein

<400> SEQUENCE: 47

Phe Leu Cys Gln Tyr Cys Ala Gln Arg Phe Gly Arg Lys Asp His Leu
1               5                   10                  15
Thr Arg His Met Lys His Ser His
            20

<210> SEQ ID NO 48
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 48

Cys Arg Cys Asn Glu Cys Gly Lys Ser Phe Ser Arg Arg Asp His Leu
1               5                   10                  15
Val Arg His Gln Arg Thr His
            20

<210> SEQ ID NO 49
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 49
```

```
Phe Gln Cys Lys Thr Cys Gln Arg Lys Phe Ser Arg Ser Asp His Leu
1               5                   10                  15

Lys Thr His Thr Arg Thr His
            20

<210> SEQ ID NO 50
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 50

Phe Ala Cys Glu Val Cys Gly Val Arg Phe Thr Arg Asn Asp Lys Leu
1               5                   10                  15

Lys Ile His Met Arg Lys His
            20

<210> SEQ ID NO 51
<211> LENGTH: 25
<212> TYPE: PRT
<213> ORGANISM: Artificial Sequence
<220> FEATURE:
<223> OTHER INFORMATION: metal ion binding motif of zinc finger protein

<400> SEQUENCE: 51

Tyr Val Cys Asp Val Glu Gly Cys Thr Trp Lys Phe Ala Arg Ser Asp
1               5                   10                  15

Lys Leu Asn Arg His Lys Lys Arg His
            20                  25

<210> SEQ ID NO 52
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 52

Tyr Lys Cys Met Glu Cys Gly Lys Ala Phe Asn Arg Arg Ser His Leu
1               5                   10                  15

Thr Arg His Gln Arg Ile His
            20

<210> SEQ ID NO 53
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 53

Tyr Ile Cys Arg Lys Cys Gly Arg Gly Phe Ser Arg Lys Ser Asn Leu
1               5                   10                  15

Ile Arg His Gln Arg Thr His
            20

<210> SEQ ID NO 54
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 54
```

Tyr Glu Cys Lys Glu Cys Gly Lys Ala Phe Ser Ser Gly Ser Asn Phe
1               5                   10                  15

Thr Arg His Gln Arg Ile His
            20

<210> SEQ ID NO 55
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 55

Phe His Cys Gly Tyr Cys Glu Lys Ser Phe Ser Val Lys Asp Tyr Leu
1               5                   10                  15

Thr Lys His Ile Arg Thr His
            20

<210> SEQ ID NO 56
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 56

Tyr Glu Cys Asp His Cys Gly Lys Ala Phe Ser Val Ser Ser Asn Leu
1               5                   10                  15

Asn Val His Arg Arg Ile His
            20

<210> SEQ ID NO 57
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 57

Tyr Thr Cys Lys Gln Cys Gly Lys Ala Phe Ser Val Ser Ser Ser Leu
1               5                   10                  15

Arg Arg His Glu Thr Thr His
            20

<210> SEQ ID NO 58
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 58

Tyr Glu Cys Asn Tyr Cys Gly Lys Thr Phe Ser Val Ser Ser Thr Leu
1               5                   10                  15

Ile Arg His Gln Arg Ile His
            20

<210> SEQ ID NO 59
<211> LENGTH: 23
<212> TYPE: PRT
<213> ORGANISM: Artificial Sequence
<220> FEATURE:
<223> OTHER INFORMATION: metal ion binding motif of zinc finger protein

```
<400> SEQUENCE: 59

Tyr Arg Cys Glu Glu Cys Gly Lys Ala Phe Arg Trp Pro Ser Asn Leu
1               5                   10                  15

Thr Arg His Lys Arg Ile His
            20

<210> SEQ ID NO 60
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 60

Phe Ala Cys Asp Ile Cys Gly Arg Lys Phe Ala Arg Ser Asp Glu Arg
1               5                   10                  15

Lys Arg His Thr Lys Ile His
            20

<210> SEQ ID NO 61
<211> LENGTH: 23
<212> TYPE: PRT
<213> ORGANISM: Artificial Sequence
<220> FEATURE:
<223> OTHER INFORMATION: metal ion binding motif of zinc finger protein

<400> SEQUENCE: 61

Cys Pro Val Glu Ser Cys Asp Arg Arg Phe Ser Arg Ser Asp Glu Leu
1               5                   10                  15

Thr Arg His Ile Arg Ile His
            20

<210> SEQ ID NO 62
<211> LENGTH: 21
<212> TYPE: PRT
<213> ORGANISM: Artificial Sequence
<220> FEATURE:
<223> OTHER INFORMATION: metal ion binding motif of zinc finger protein

<400> SEQUENCE: 62

Cys Asp Ile Cys Gly Arg Lys Phe Ala Arg Ser Asp Glu Arg Lys Arg
1               5                   10                  15

His Thr Lys Ile His
            20

<210> SEQ ID NO 63
<211> LENGTH: 54
<212> TYPE: PRT
<213> ORGANISM: Artificial Sequence
<220> FEATURE:
<223> OTHER INFORMATION: CadC protein

<400> SEQUENCE: 63

Cys Glu Ile Phe Cys Tyr Asp Glu Glu Lys Val Asn Arg Ile Gln Gly
1               5                   10                  15

Asp Leu Gln Thr Val Asp Ile Ser Gly Val Ser Gln Ile Leu Lys Ala
            20                  25                  30

Ile Ala Asp Glu Asn Arg Ala Lys Ile Thr Tyr Ala Leu Cys Gln Asp
        35                  40                  45

Glu Glu Leu Cys Val Cys
    50
```

```
<210> SEQ ID NO 64
<211> LENGTH: 54
<212> TYPE: PRT
<213> ORGANISM: Artificial Sequence
<220> FEATURE:
<223> OTHER INFORMATION: AztR protein

<400> SEQUENCE: 64

Cys Asp Thr His Leu Val His Leu Asp Asn Val Arg Ser Ser Gln Ala
1               5                   10                  15

Gln Ile Leu Pro Thr Asp Lys Ala Gln Gln Met Ala Glu Ile Phe Gly
            20                  25                  30

Val Leu Ala Asp Thr Asn Arg Ile Arg Leu Leu Ser Ala Leu Ala Ser
        35                  40                  45

Ser Glu Leu Cys Val Cys
    50

<210> SEQ ID NO 65
<211> LENGTH: 54
<212> TYPE: PRT
<213> ORGANISM: Artificial Sequence
<220> FEATURE:
<223> OTHER INFORMATION: ZiaR protein

<400> SEQUENCE: 65

Cys Asp Gln Pro Leu Val His Leu Glu Gln Val Arg Gln Val Gln Pro
1               5                   10                  15

Glu Val Met Ser Leu Asp Gln Ala Gln Gln Met Ala Glu Phe Phe Ser
            20                  25                  30

Ala Leu Ala Asp Pro Ser Arg Leu Arg Leu Met Ser Ala Leu Ala Arg
        35                  40                  45

Gln Glu Leu Cys Val Cys
    50

<210> SEQ ID NO 66
<211> LENGTH: 55
<212> TYPE: PRT
<213> ORGANISM: Artificial Sequence
<220> FEATURE:
<223> OTHER INFORMATION: BxmR protein

<400> SEQUENCE: 66

Cys Asp Arg Ala His Leu Val Asp Cys Ser Arg Val Gly Asp Ile Gln
1               5                   10                  15

Thr Gln Val Leu Asn Thr Ala Lys Ala Gln Arg Met Ala Glu Phe Phe
            20                  25                  30

Ser Leu Leu Gly Asp Ala Asn Arg Leu Arg Val Val Ser Val Leu Ala
        35                  40                  45

Lys Gln Glu Leu Cys Val Cys
    50                  55

<210> SEQ ID NO 67
<211> LENGTH: 26
<212> TYPE: PRT
<213> ORGANISM: Artificial Sequence
<220> FEATURE:
<223> OTHER INFORMATION: ArsR protein

<400> SEQUENCE: 67

Leu Ser Asp Glu Thr Arg Leu Gly Ile Val Leu Leu Leu Arg Glu Met
1               5                   10                  15

Gly Glu Leu Cys Val Cys Asp Leu Cys Met
```

-continued

<210> SEQ ID NO 68
<211> LENGTH: 41
<212> TYPE: PRT
<213> ORGANISM: Artificial Sequence
<220> FEATURE:
<223> OTHER INFORMATION: ArsR protein

<400> SEQUENCE: 68

Cys Cys Thr Leu Ala Thr Gly Pro Leu Ser Ser Asp Glu Ser Glu His
 1               5                  10                  15

Tyr Ala Asp Leu Phe Lys Val Leu Gly Asp Pro Val Arg Leu Arg Ile
            20                  25                  30

Leu Ser Gln Leu Ala Ala Gly Gly Cys
        35                  40

<210> SEQ ID NO 69
<211> LENGTH: 26
<212> TYPE: PRT
<213> ORGANISM: Artificial Sequence
<220> FEATURE:
<223> OTHER INFORMATION: ArsR protein

<400> SEQUENCE: 69

Tyr Arg Ala Ala Met Pro Val Val Arg Ala Leu Val Ala Tyr Leu Thr
 1               5                  10                  15

Glu Asn Cys Cys His Gly Thr Arg Asp Cys
            20                  25

<210> SEQ ID NO 70
<211> LENGTH: 46
<212> TYPE: PRT
<213> ORGANISM: Artificial Sequence
<220> FEATURE:
<223> OTHER INFORMATION: CmtR protein

<400> SEQUENCE: 70

Cys Leu Arg Gly Cys Gly Leu Val Val Ala Thr Tyr Glu Gly Arg Gln
 1               5                  10                  15

Val Arg Tyr Ala Leu Ala Asp Ser His Leu Ala Arg Ala Leu Gly Glu
            20                  25                  30

Leu Val Gln Val Val Leu Ala Val Asp Thr Asp Gln Pro Cys
        35                  40                  45

<210> SEQ ID NO 71
<211> LENGTH: 55
<212> TYPE: PRT
<213> ORGANISM: Artificial Sequence
<220> FEATURE:
<223> OTHER INFORMATION: CmtR protein

<400> SEQUENCE: 71

Cys Leu Arg Asp Cys Gly Leu Val Val Thr Val Pro Asp Gly Arg Arg
 1               5                  10                  15

Ser Arg Tyr Glu Leu Ala Asp Glu Arg Leu Gly His Ala Leu Asp Asp
            20                  25                  30

Leu Arg Ala Ala Val Val Ala Val Asp Ala Asp Arg Thr Cys Pro Asp
        35                  40                  45

Ala Asp Glu Leu Glu Cys Cys
    50                  55

```
<210> SEQ ID NO 72
<211> LENGTH: 31
<212> TYPE: PRT
<213> ORGANISM: Artificial Sequence
<220> FEATURE:
<223> OTHER INFORMATION: E.coli ZntA

<400> SEQUENCE: 72

Val Ser Gly Met Asp Cys Ala Ala Cys Ala Arg Lys Val Glu Asn Ala
1               5                   10                  15

Val Arg Gln Leu Ala Gly Val Asn Gln Val Gln Val Leu Phe Ala
            20                  25                  30

<210> SEQ ID NO 73
<211> LENGTH: 31
<212> TYPE: PRT
<213> ORGANISM: Artificial Sequence
<220> FEATURE:
<223> OTHER INFORMATION: Tn501 MerP

<400> SEQUENCE: 73

Val Pro Gly Met Thr Cys Ser Ala Cys Pro Ile Thr Val Lys Lys Ala
1               5                   10                  15

Ile Ser Glu Val Glu Gly Val Ser Lys Val Asp Val Thr Phe Glu
            20                  25                  30

<210> SEQ ID NO 74
<211> LENGTH: 30
<212> TYPE: PRT
<213> ORGANISM: Artificial Sequence
<220> FEATURE:
<223> OTHER INFORMATION: Tn501 MerA

<400> SEQUENCE: 74

Ile Thr Gly Met Thr Cys Asp Ser Cys Ala Ala His Val Lys Glu Ala
1               5                   10                  15

Leu Glu Lys Val Pro Gly Val Gln Ser Ala Leu Val Ser Tyr
            20                  25                  30

<210> SEQ ID NO 75
<211> LENGTH: 31
<212> TYPE: PRT
<213> ORGANISM: Artificial Sequence
<220> FEATURE:
<223> OTHER INFORMATION: S.aureus CadA

<400> SEQUENCE: 75

Val Gln Gly Phe Thr Cys Ala Asn Cys Ala Gly Lys Phe Glu Lys Asn
1               5                   10                  15

Val Lys Lys Ile Pro Gly Val Gln Asp Ala Lys Val Asn Phe Gly
            20                  25                  30

<210> SEQ ID NO 76
<211> LENGTH: 31
<212> TYPE: PRT
<213> ORGANISM: Artificial Sequence
<220> FEATURE:
<223> OTHER INFORMATION: Human Menkes

<400> SEQUENCE: 76

Val Glu Gly Met Thr Cys Asn Ser Cys Val Trp Thr Ile Glu Gln Gln
1               5                   10                  15

Ile Gly Lys Val Asn Gly Glu His His Ile Lys Val Ser Leu Glu
            20                  25                  30
```

<210> SEQ ID NO 77
<211> LENGTH: 29
<212> TYPE: PRT
<213> ORGANISM: Artificial Sequence
<220> FEATURE:
<223> OTHER INFORMATION: Yeast Atx1

<400> SEQUENCE: 77

Val Val Met Thr Cys Ser Gly Cys Ser Gly Ala Val Asn Lys Val Leu
1               5                   10                  15

Thr Lys Leu Glu Pro Asp Val Ser Lys Ile Asp Ile Ser
            20                  25

<210> SEQ ID NO 78
<211> LENGTH: 24
<212> TYPE: PRT
<213> ORGANISM: Artificial Sequence
<220> FEATURE:
<223> OTHER INFORMATION: Rat Wilsons

<400> SEQUENCE: 78

Gly Met Thr Cys Ala Ser Cys Val Ala Asn Ile Glu Arg Asn Leu Arg
1               5                   10                  15

Arg Glu Glu Gly Ile Tyr Ser Val
            20

<210> SEQ ID NO 79
<211> LENGTH: 30
<212> TYPE: PRT
<213> ORGANISM: Artificial Sequence
<220> FEATURE:
<223> OTHER INFORMATION: Hum Wilsons

<400> SEQUENCE: 79

Tyr Glu Gly Met Thr Cys Gln Ser Cys Val Ser Ser Ile Glu Gly Lys
1               5                   10                  15

Tyr Arg Lys Leu Gln Gly Val Val Arg Tyr Lys Val Ser Leu
            20                  25                  30

<210> SEQ ID NO 80
<211> LENGTH: 29
<212> TYPE: PRT
<213> ORGANISM: Artificial Sequence
<220> FEATURE:
<223> OTHER INFORMATION: Rice Cu ATPase

<400> SEQUENCE: 80

Gly Met Ser Cys Gln Gly Cys Ala Gly Ala Val Arg Arg Val Leu Thr
1               5                   10                  15

Lys Met Glu Gly Val Glu Thr Phe Asp Ile Asp Met Glu
            20                  25

<210> SEQ ID NO 81
<211> LENGTH: 31
<212> TYPE: PRT
<213> ORGANISM: Artificial Sequence
<220> FEATURE:
<223> OTHER INFORMATION: H.pylori Cu ATPase

<400> SEQUENCE: 81

Val Pro Ser Ile Thr Cys Ser His Cys Val Asp Lys Ile Glu Lys Phe
1               5                   10                  15

Val Gly Glu Ile Glu Gly Val Ser Phe Ile Asp Ala Asn Val Glu
            20                  25                  30

<210> SEQ ID NO 82
<211> LENGTH: 52
<212> TYPE: PRT
<213> ORGANISM: Artificial Sequence
<220> FEATURE:
<223> OTHER INFORMATION: Ran1

<400> SEQUENCE: 82

```
Val Thr Gly Met Thr Cys Ala Ala Cys Ser Asn Ser Val Glu Ala Ala
1               5                   10                  15

Leu Met Asn Val Asn Gly Val Asp Val Gly Gly Met Thr Cys Gly Gly
            20                  25                  30

Cys Ser Ala Ser Val Lys Lys Leu Leu Glu Ser Gln Pro Cys Val Ala
        35                  40                  45

Ser Ala Ser Val
        50
```

<210> SEQ ID NO 83
<211> LENGTH: 23
<212> TYPE: PRT
<213> ORGANISM: Artificial Sequence
<220> FEATURE:
<223> OTHER INFORMATION: Cpx89

<400> SEQUENCE: 83

```
Val Ser Gly Met Val Cys Ala Ala Cys Ser Thr Ala Val Glu Asn Ala
1               5                   10                  15

Leu Leu Ser Cys Ser Gly Val
            20
```

<210> SEQ ID NO 84
<211> LENGTH: 22
<212> TYPE: PRT
<213> ORGANISM: Artificial Sequence
<220> FEATURE:
<223> OTHER INFORMATION: Paa1

<400> SEQUENCE: 84

```
Asp Val Gly Gly Met Thr Cys Gly Gly Cys Ser Ala Ser Val Lys Lys
1               5                   10                  15

Ile Leu Glu Ser Gln Pro
            20
```

<210> SEQ ID NO 85
<211> LENGTH: 28
<212> TYPE: PRT
<213> ORGANISM: Artificial Sequence
<220> FEATURE:
<223> OTHER INFORMATION: Cpx1184

<400> SEQUENCE: 85

```
Asp Val Gly Gly Met Lys Cys Gly Gly Cys Val Glu His Val Lys Lys
1               5                   10                  15

Ile Leu Glu Glu Gln Phe Gly Val Thr Ser Ala Ser
            20                  25
```

<210> SEQ ID NO 86
<211> LENGTH: 26
<212> TYPE: PRT
<213> ORGANISM: Artificial Sequence
<220> FEATURE:
<223> OTHER INFORMATION: Metal ion binding motif -continued

```
<400> SEQUENCE: 86

Pro Tyr Lys Cys Pro Glu Cys Gly Lys Ser Phe Ser Gln Lys Ser Ala
1               5                   10                  15

Leu Val Lys His Gln Arg Thr His Thr Cys
            20                  25

<210> SEQ ID NO 87
<211> LENGTH: 26
<212> TYPE: PRT
<213> ORGANISM: Artificial Sequence
<220> FEATURE:
<223> OTHER INFORMATION: Metal ion binding motif

<400> SEQUENCE: 87

Pro Tyr Lys Cys Pro Glu Cys Gly Lys Ser Phe Ser Gln Lys Ser Ala
1               5                   10                  15

Leu Val Lys His Gln Arg Thr His Thr Met
            20                  25

<210> SEQ ID NO 88
<211> LENGTH: 26
<212> TYPE: PRT
<213> ORGANISM: Artificial Sequence
<220> FEATURE:
<223> OTHER INFORMATION: Metal ion binding motif

<400> SEQUENCE: 88

Pro Tyr Lys Cys Pro Glu Cys Gly Lys Ser Phe Ser Gln Lys Ser Ala
1               5                   10                  15

Leu Val Lys His Gln Arg Thr His Thr Cys
            20                  25

<210> SEQ ID NO 89
<211> LENGTH: 26
<212> TYPE: PRT
<213> ORGANISM: Artificial Sequence
<220> FEATURE:
<223> OTHER INFORMATION: Metal ion binding motif

<400> SEQUENCE: 89

Pro Tyr Lys Cys Pro Glu Cys Gly Lys Ser Phe Ser Gln Lys Ser Ala
1               5                   10                  15

Leu Val Lys His Gln Arg Thr His Thr His
            20                  25

<210> SEQ ID NO 90
<211> LENGTH: 26
<212> TYPE: PRT
<213> ORGANISM: Artificial Sequence
<220> FEATURE:
<223> OTHER INFORMATION: Metal ion binding motif

<400> SEQUENCE: 90

Pro Tyr Lys Cys Pro Glu Cys Gly Lys Ser Phe Ser Gln Lys Ser Ala
1               5                   10                  15

Leu Val Lys His Gln Arg Thr His Thr His
            20                  25

<210> SEQ ID NO 91
<211> LENGTH: 22
<212> TYPE: PRT
<213> ORGANISM: Artificial Sequence
<220> FEATURE:
<223> OTHER INFORMATION: Metal ion binding motif
```

```
<400> SEQUENCE: 91

Pro Tyr Lys Cys Pro Glu Cys Gly Lys Ser Phe Ser Gln Lys Ser Ala
1               5                   10                  15

Leu Val Lys His Gln Arg
            20

<210> SEQ ID NO 92
<211> LENGTH: 30
<212> TYPE: PRT
<213> ORGANISM: Artificial Sequence
<220> FEATURE:
<223> OTHER INFORMATION: metal ion-binding peptide motif

<400> SEQUENCE: 92

Gly Leu Lys Ala Leu Glu Glu Lys Cys Lys Ala Leu Glu Glu Lys Leu
1               5                   10                  15

Lys Ala Leu Glu Glu Lys Leu Lys Ala Leu Glu Glu Lys Gly
            20                  25                  30

<210> SEQ ID NO 93
<211> LENGTH: 30
<212> TYPE: PRT
<213> ORGANISM: Artificial Sequence
<220> FEATURE:
<223> OTHER INFORMATION: metal ion-binding peptide motif

<400> SEQUENCE: 93

Gly Leu Lys Ala Leu Glu Glu Lys Leu Lys Ala Leu Glu Glu Lys Leu
1               5                   10                  15

Lys Ala Cys Glu Glu Lys Leu Lys Ala Leu Glu Glu Lys Gly
            20                  25                  30

<210> SEQ ID NO 94
<211> LENGTH: 30
<212> TYPE: PRT
<213> ORGANISM: Artificial Sequence
<220> FEATURE:
<223> OTHER INFORMATION: metal ion-binding peptide motif

<400> SEQUENCE: 94

Gly Leu Lys Ala Leu Glu Glu Lys Cys Lys Ala Leu Glu Glu Lys Leu
1               5                   10                  15

Lys Ala Cys Glu Glu Lys Leu Lys Ala Leu Glu Glu Lys Gly
            20                  25                  30

<210> SEQ ID NO 95
<211> LENGTH: 30
<212> TYPE: PRT
<213> ORGANISM: Artificial Sequence
<220> FEATURE:
<223> OTHER INFORMATION: metal ion-binding peptide motif

<400> SEQUENCE: 95

Gly Leu Lys Ala Leu Glu Glu Lys Leu Lys Ala Leu Glu Glu Lys Cys
1               5                   10                  15

Lys Ala Leu Glu Glu Lys Leu Lys Ala Leu Glu Glu Lys Gly
            20                  25                  30

<210> SEQ ID NO 96
<211> LENGTH: 30
<212> TYPE: PRT
<213> ORGANISM: Artificial Sequence
<220> FEATURE:
```

<223> OTHER INFORMATION: metal ion-binding peptide motif

<400> SEQUENCE: 96

Gly Leu Lys Ala Leu Glu Glu Lys Leu Lys Ala Leu Glu Glu Lys Leu
1               5                   10                  15

Lys Ala Leu Glu Glu Lys Cys Lys Ala Leu Glu Glu Lys Gly
            20                  25                  30

<210> SEQ ID NO 97
<211> LENGTH: 37
<212> TYPE: PRT
<213> ORGANISM: Artificial Sequence
<220> FEATURE:
<223> OTHER INFORMATION: metal ion-binding peptide motif

<400> SEQUENCE: 97

Gly Leu Lys Ala Leu Glu Glu Lys Leu Lys Ala Leu Glu Glu Lys Leu
1               5                   10                  15

Lys Ala Leu Glu Glu Lys Leu Lys Ala Ala Glu Glu Lys Cys Lys Ala
            20                  25                  30

Leu Glu Glu Lys Gly
        35

<210> SEQ ID NO 98
<211> LENGTH: 37
<212> TYPE: PRT
<213> ORGANISM: Artificial Sequence
<220> FEATURE:
<223> OTHER INFORMATION: metal ion-binding peptide motif

<400> SEQUENCE: 98

Gly Leu Lys Ala Leu Glu Glu Lys Leu Lys Ala Leu Glu Glu Lys Cys
1               5                   10                  15

Lys Ala Leu Glu Glu Lys Leu Lys Ala Ala Glu Glu Lys Cys Lys Ala
            20                  25                  30

Leu Glu Glu Lys Gly
        35

<210> SEQ ID NO 99
<211> LENGTH: 34
<212> TYPE: PRT
<213> ORGANISM: Artificial Sequence
<220> FEATURE:
<223> OTHER INFORMATION: metal ion-binding peptide motif

<400> SEQUENCE: 99

Leu Tyr Ala Leu Glu Lys Glu Leu Gly Ala Leu Glu Lys Glu Leu Ala
1               5                   10                  15

Cys Leu Glu Lys Glu Leu Gly Ala Leu Glu Lys Glu Leu Tyr Ala Leu
            20                  25                  30

Glu Lys

<210> SEQ ID NO 100
<211> LENGTH: 35
<212> TYPE: PRT
<213> ORGANISM: Artificial Sequence
<220> FEATURE:
<223> OTHER INFORMATION: metal ion-binding peptide motif

<400> SEQUENCE: 100

Lys Leu Tyr Ala Leu Lys Glu Lys Leu Gly Ala Leu Lys Glu Lys Leu
1               5                   10                  15

```
Ala Cys Leu Lys Glu Lys Leu Gly Ala Leu Lys Glu Lys Leu Tyr Ala
            20                  25                  30

Leu Lys Glu
        35

<210> SEQ ID NO 101
<211> LENGTH: 35
<212> TYPE: PRT
<213> ORGANISM: Artificial Sequence
<220> FEATURE:
<223> OTHER INFORMATION: metal ion-binding peptide motif

<400> SEQUENCE: 101

Glu Leu Tyr Ala Leu Glu Lys Glu Leu Gly Ala Leu Glu Lys Glu Leu
1               5                   10                  15

Ala Cys Leu Lys Glu Lys Leu Gly Ala Leu Lys Glu Lys Leu Tyr Ala
            20                  25                  30

Leu Lys Glu
        35

<210> SEQ ID NO 102
<211> LENGTH: 35
<212> TYPE: PRT
<213> ORGANISM: Artificial Sequence
<220> FEATURE:
<223> OTHER INFORMATION: metal ion-binding peptide motif

<400> SEQUENCE: 102

Lys Leu Tyr Ala Leu Lys Glu Lys Leu Gly Ala Leu Lys Glu Lys Leu
1               5                   10                  15

Ala Cys Leu Glu Lys Glu Leu Gly Ala Leu Glu Lys Glu Leu Tyr Ala
            20                  25                  30

Leu Glu Lys
        35

<210> SEQ ID NO 103
<211> LENGTH: 7
<212> TYPE: PRT
<213> ORGANISM: Artificial Sequence
<220> FEATURE:
<223> OTHER INFORMATION: Cys2His2 metal ion binding motif
<220> FEATURE:
<221> NAME/KEY: misc_feature
<222> LOCATION: (2)..(2)
<223> OTHER INFORMATION: Xaa is a sequence of 2-4 amino acid residues,
      each of which independently may be any amino acid residue other
      than Cys
<220> FEATURE:
<221> NAME/KEY: misc_feature
<222> LOCATION: (4)..(4)
<223> OTHER INFORMATION: Xaa is a sequence of 12 amino acid residues,
      each of which independently may be any amino acid residue other
      than Cys
<220> FEATURE:
<221> NAME/KEY: misc_feature
<222> LOCATION: (6)..(6)
<223> OTHER INFORMATION: Xaa is a sequence of 3-5 amino acid residues,
      each of which independently may be any amino acid residue other
      than Cys

<400> SEQUENCE: 103

Cys Xaa Cys Xaa His Xaa His
1               5

<210> SEQ ID NO 104
<211> LENGTH: 15
<212> TYPE: PRT
```

```
<213> ORGANISM: Artificial Sequence
<220> FEATURE:
<223> OTHER INFORMATION: C4 class metal ion binding motif
<220> FEATURE:
<221> NAME/KEY: misc_feature
<222> LOCATION: (2)..(2)
<223> OTHER INFORMATION: Xaa is a sequence of 2 amino acid residues,
      each of which independently may be any amino acid residue other
      than Cys
<220> FEATURE:
<221> NAME/KEY: misc_feature
<222> LOCATION: (4)..(4)
<223> OTHER INFORMATION: Xaa is a sequence of 1-10 amino acid residues,
      each of which independently may be any amino acid residue other
      than Cys
<220> FEATURE:
<221> NAME/KEY: misc_feature
<222> LOCATION: (6)..(6)
<223> OTHER INFORMATION: Xaa is a sequence of 2 amino acid residues,
      each of which independently may be any amino acid residue other
      than Cys
<220> FEATURE:
<221> NAME/KEY: misc_feature
<222> LOCATION: (8)..(8)
<223> OTHER INFORMATION: Xaa is a sequence of 1-10 amino acid residues,
      each of which independently may be any amino acid residue other
      than Cys
<220> FEATURE:
<221> NAME/KEY: misc_feature
<222> LOCATION: (10)..(10)
<223> OTHER INFORMATION: Xaa is a sequence of 2 amino acid residues,
      each of which independently may be any amino acid residue other
      than Cys
<220> FEATURE:
<221> NAME/KEY: misc_feature
<222> LOCATION: (12)..(12)
<223> OTHER INFORMATION: Xaa is a sequence of 1-10 amino acid residues,
      each of which independently may be any amino acid residue other
      than Cys
<220> FEATURE:
<221> NAME/KEY: misc_feature
<222> LOCATION: (14)..(14)
<223> OTHER INFORMATION: Xaa is a sequence of 2 amino acid residues,
      each of which independently may be any amino acid residue other
      than Cys

<400> SEQUENCE: 104

Cys Xaa Cys Xaa Cys Xaa Cys Xaa Cys Xaa Cys Xaa Cys Xaa Cys
1               5                   10                  15

<210> SEQ ID NO 105
<211> LENGTH: 11
<212> TYPE: PRT
<213> ORGANISM: Artificial Sequence
<220> FEATURE:
<223> OTHER INFORMATION: C6 class metal ion binding motif
<220> FEATURE:
<221> NAME/KEY: misc_feature
<222> LOCATION: (2)..(2)
<223> OTHER INFORMATION: Xaa is a sequence of 2 amino acid residues,
      each of which independently may be any amino acid residue other
      than Cys
<220> FEATURE:
<221> NAME/KEY: misc_feature
<222> LOCATION: (4)..(4)
<223> OTHER INFORMATION: Xaa is a sequence of 6 amino acid residues,
      each of which independently may be any amino acid residue other
      than Cys
<220> FEATURE:
<221> NAME/KEY: misc_feature
<222> LOCATION: (6)..(6)
<223> OTHER INFORMATION: Xaa is a sequence of 5-12 amino acid residues,
      each of which independently may be any amino acid residue other
      than Cys
<220> FEATURE:
<221> NAME/KEY: misc_feature
<222> LOCATION: (8)..(8)
```

```
<223> OTHER INFORMATION: Xaa is a sequence of 2 amino acid residues,
      each of which independently may be any amino acid residue other
      than Cys
<220> FEATURE:
<221> NAME/KEY: misc_feature
<222> LOCATION: (10)..(10)
<223> OTHER INFORMATION: Xaa is a sequence of 6-8 amino acid residues,
      each of which independently may be any amino acid residue other
      than Cys

<400> SEQUENCE: 105

Cys Xaa Cys Xaa Cys Xaa Cys Xaa Cys Xaa Cys
1               5                   10

<210> SEQ ID NO 106
<211> LENGTH: 4
<212> TYPE: PRT
<213> ORGANISM: Artificial Sequence
<220> FEATURE:
<223> OTHER INFORMATION: CXC metal ion binding motif
<220> FEATURE:
<221> NAME/KEY: misc_feature
<222> LOCATION: (2)..(2)
<223> OTHER INFORMATION: Xaa is any amino acid residue other than Cys
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa is any amino acid residue other than Cys

<400> SEQUENCE: 106

Cys Xaa Xaa Cys
1

<210> SEQ ID NO 107
<211> LENGTH: 6
<212> TYPE: PRT
<213> ORGANISM: Artificial Sequence
<220> FEATURE:
<223> OTHER INFORMATION: metal ion binding motif
<220> FEATURE:
<221> NAME/KEY: misc_feature
<222> LOCATION: (2)..(2)
<223> OTHER INFORMATION: Xaa is any amino acid residue other than Cys
<220> FEATURE:
<221> NAME/KEY: misc_feature
<222> LOCATION: (4)..(4)
<223> OTHER INFORMATION: Xaa is any amino acid residue other than Cys
<220> FEATURE:
<221> NAME/KEY: misc_feature
<222> LOCATION: (5)..(5)
<223> OTHER INFORMATION: Xaa is any amino acid residue other than Cys

<400> SEQUENCE: 107

Met Xaa Cys Xaa Xaa Cys
1               5

<210> SEQ ID NO 108
<211> LENGTH: 7
<212> TYPE: PRT
<213> ORGANISM: Artificial Sequence
<220> FEATURE:
<223> OTHER INFORMATION: metal ion binding motif

<400> SEQUENCE: 108

Cys Gln Cys Gln Cys Ala Cys
1               5
```

```
<210> SEQ ID NO 109
<211> LENGTH: 27
<212> TYPE: PRT
<213> ORGANISM: Artificial Sequence
<220> FEATURE:
<223> OTHER INFORMATION: metal ion binding motif
<220> FEATURE:
<221> NAME/KEY: misc_feature
<222> LOCATION: (2)..(2)
<223> OTHER INFORMATION: Xaa is any amino acid
<220> FEATURE:
<221> NAME/KEY: misc_feature
<222> LOCATION: (3)..(3)
<223> OTHER INFORMATION: Xaa is any amino acid
<220> FEATURE:
<221> NAME/KEY: misc_feature
<222> LOCATION: (8)..(8)
<223> OTHER INFORMATION: Xaa is a sequence of 21-28 amino acid residues,
      each of which independently may be any amino acid residue other
      than Cys
<220> FEATURE:
<221> NAME/KEY: misc_feature
<222> LOCATION: (10)..(10)
<223> OTHER INFORMATION: Xaa is any amino acid
<220> FEATURE:
<221> NAME/KEY: misc_feature
<222> LOCATION: (17)..(17)
<223> OTHER INFORMATION: Xaa is any amino acid
<220> FEATURE:
<221> NAME/KEY: misc_feature
<222> LOCATION: (23)..(23)
<223> OTHER INFORMATION: Xaa is a sequence of 18-27 amino acid residues,
      each of which independently may be any amino acid residue other
      than Cys
<220> FEATURE:
<221> NAME/KEY: misc_feature
<222> LOCATION: (25)..(25)
<223> OTHER INFORMATION: Xaa is any amino acid
<220> FEATURE:
<221> NAME/KEY: misc_feature
<222> LOCATION: (26)..(26)
<223> OTHER INFORMATION: Xaa is any amino acid

<400> SEQUENCE: 109

His Xaa Xaa Trp Phe Tyr Leu Xaa Cys Xaa Leu Phe Met Val Ile Gly
1               5                   10                  15

Xaa Trp Phe Leu Val Ile Xaa His Xaa Xaa His
            20                  25

<210> SEQ ID NO 110
<211> LENGTH: 6
<212> TYPE: PRT
<213> ORGANISM: Artificial Sequence
<220> FEATURE:
<223> OTHER INFORMATION: metal ion binding motif
<220> FEATURE:
<221> NAME/KEY: misc_feature
<222> LOCATION: (2)..(2)
<223> OTHER INFORMATION: Xaa is any amino acid
<220> FEATURE:
<221> NAME/KEY: misc_feature
<222> LOCATION: (4)..(4)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is any amino acid

<400> SEQUENCE: 110

Met Xaa Cys Xaa Xaa Cys
1               5

<210> SEQ ID NO 111
<211> LENGTH: 5
```

-continued

```
<212> TYPE: PRT
<213> ORGANISM: Artificial Sequence
<220> FEATURE:
<223> OTHER INFORMATION: metal ion binding motif

<400> SEQUENCE: 111

Ala Cys Gly His Ala
1               5

<210> SEQ ID NO 112
<211> LENGTH: 12
<212> TYPE: PRT
<213> ORGANISM: Artificial Sequence
<220> FEATURE:
<223> OTHER INFORMATION: metal ion binding motif

<400> SEQUENCE: 112

Gln Cys Gly Val Cys Gly Lys Cys Ile Ala Cys Lys
1               5                   10

<210> SEQ ID NO 113
<211> LENGTH: 26
<212> TYPE: PRT
<213> ORGANISM: Artificial Sequence
<220> FEATURE:
<223> OTHER INFORMATION: metal ion binding motif

<400> SEQUENCE: 113

Pro Tyr Lys Cys Pro Glu Cys Gly Lys Ser Phe Ser Gln Lys Ser Ala
1               5                   10                  15

Leu Val Lys His Gln Arg Thr His Thr His
            20                  25

<210> SEQ ID NO 114
<211> LENGTH: 7
<212> TYPE: PRT
<213> ORGANISM: Artificial Sequence
<220> FEATURE:
<223> OTHER INFORMATION: metal ion binding motif unit structure,
      optionally repeated 2-5 times

<400> SEQUENCE: 114

Leu Lys Ala Leu Glu Glu Lys
1               5

<210> SEQ ID NO 115
<211> LENGTH: 47
<212> TYPE: PRT
<213> ORGANISM: Artificial Sequence
<220> FEATURE:
<223> OTHER INFORMATION: metal ion binding motif

<400> SEQUENCE: 115

Gln Cys Gly Val Cys Gly Lys Cys Ile Ala Cys Lys Glu Leu Tyr Ala
1               5                   10                  15

Leu Glu Lys Glu Leu Gly Ala Leu Glu Lys Glu Leu Ala Cys Leu Glu
            20                  25                  30

Lys Glu Leu Gly Ala Leu Glu Lys Glu Leu Tyr Ala Leu Glu Lys
        35                  40                  45

<210> SEQ ID NO 116
<211> LENGTH: 30
<212> TYPE: DNA
<213> ORGANISM: Artificial Sequence
<220> FEATURE:
<223> OTHER INFORMATION: XhoHH forward primer
```

```
<400> SEQUENCE: 116 gggggggctcg agaccatggg ttggagctgt                               30

<210> SEQ ID NO 117
<211> LENGTH: 30
<212> TYPE: DNA
<213> ORGANISM: Artificial Sequence
<220> FEATURE:
<223> OTHER INFORMATION: HHNot reverse primer

<400> SEQUENCE: 117
gcggccggcc gctcaacaac ccggagacag                                30

<210> SEQ ID NO 118
<211> LENGTH: 36
<212> TYPE: DNA
<213> ORGANISM: Artificial Sequence
<220> FEATURE:
<223> OTHER INFORMATION: HHNot reverse primer

<400> SEQUENCE: 118
gcggccggcc gctcaacagc cacaacccgg agacag                         36

<210> SEQ ID NO 119
<211> LENGTH: 10
<212> TYPE: PRT
<213> ORGANISM: Artificial Sequence
<220> FEATURE:
<223> OTHER INFORMATION: metal ion binding motif

<400> SEQUENCE: 119

Ala Cys His Gly Ala Ala Cys Gly His Ala
1               5                   10

<210> SEQ ID NO 120
<211> LENGTH: 30
<212> TYPE: DNA
<213> ORGANISM: Artificial Sequence
<220> FEATURE:
<223> OTHER INFORMATION: XhoHH forward primer

<400> SEQUENCE: 120 gggggggctcg agaccatggg ttggagctgt                               30

<210> SEQ ID NO 121
<211> LENGTH: 60
<212> TYPE: DNA
<213> ORGANISM: Artificial Sequence
<220> FEATURE:
<223> OTHER INFORMATION: M2 reverse primer

<400> SEQUENCE: 121
ccccgcggcc gcctaggcat ggccacaagc agcatggcca caggcgccgg gagacagaga   60

<210> SEQ ID NO 122
<211> LENGTH: 26
<212> TYPE: DNA
<213> ORGANISM: Artificial Sequence
<220> FEATURE:
<223> OTHER INFORMATION: Forward primer

<400> SEQUENCE: 122
ggtggaggtg cttgtggcca ttaagc                                    26
```

```
<210> SEQ ID NO 123
<211> LENGTH: 20
<212> TYPE: DNA
<213> ORGANISM: Artificial Sequence
<220> FEATURE:
<223> OTHER INFORMATION: Reverse primer

<400> SEQUENCE: 123
gccgggagac agagacagtg                                            20

<210> SEQ ID NO 124
<211> LENGTH: 13
<212> TYPE: PRT
<213> ORGANISM: Artificial Sequence
<220> FEATURE:
<223> OTHER INFORMATION: metal ion binding motif

<400> SEQUENCE: 124

Ala Cys Gly His Ala Gly Gly Gly Ala Cys Gly His Ala
1               5                   10

<210> SEQ ID NO 125
<211> LENGTH: 30
<212> TYPE: DNA
<213> ORGANISM: Artificial Sequence
<220> FEATURE:
<223> OTHER INFORMATION: Forward primer

<400> SEQUENCE: 125
ggtggaggtg cttgtggcca tgcctaagcg                                 30

<210> SEQ ID NO 126
<211> LENGTH: 18
<212> TYPE: DNA
<213> ORGANISM: Artificial Sequence
<220> FEATURE:
<223> OTHER INFORMATION: Reverse primer

<400> SEQUENCE: 126
agcatggcca caggcgcc                                              18

<210> SEQ ID NO 127
<211> LENGTH: 25
<212> TYPE: PRT
<213> ORGANISM: Artificial Sequence
<220> FEATURE:
<223> OTHER INFORMATION: metal ion binding motif

<400> SEQUENCE: 127

Cys Asp Ile Cys Gly Arg Lys Phe Ala Arg Ser Asp Glu Arg Lys Arg
1               5                   10                  15

His Thr Lys Ile His Leu Arg Gln Lys
            20                  25

<210> SEQ ID NO 128
<211> LENGTH: 108
<212> TYPE: DNA
<213> ORGANISM: Artificial Sequence
<220> FEATURE:
<223> OTHER INFORMATION: Z reverse primer

<400> SEQUENCE: 128
gcatgcggcc gccttacttc tgccgcaggt ggatcttggt atgcttttt cgctcgtcgg    60 atctagcaaa tttgcgtcca caaatatcgc atttgccggg agacagag              108
```

MODIFIED ANTIBODY IN WHICH MOTIF COMPRISING CYSTEINE RESIDUE IS BOUND, MODIFIED ANTIBODY-DRUG CONJUGATE COMPRISING THE MODIFIED ANTIBODY, AND PRODUCTION METHOD FOR SAME

CROSS-REFERENCE TO RELATED APPLICATIONS

This application is a U.S. national phase under the provisions of 35 U.S.C. §371 of International Patent Application No. PCT/KR13/01417 filed Feb. 22, 2013, which in turn claims priority of Korean Patent Application No. 10-2012-0019221 filed Feb. 24, 2012. The disclosures of such international patent application and Korean priority patent application are hereby incorporated herein by reference in their respective entireties, for all purposes.

TECHNICAL FIELD

The present invention relates to a modified antibody comprising a cysteine (Cys)-containing motif bound to a parent antibody, preferably the terminus of the parent antibody, more preferably the terminus of the heavy or light chain of the parent antibody, and most preferably the C-terminus of the heavy or light chain of the parent antibody, a modified antibody-drug conjugate (mADC) comprising a drug for diagnosis or treatment bound to the modified antibody, and a method for producing the modified antibody or the modified antibody-drug conjugate.

The modified antibody-drug conjugate according to the present invention can accurately deliver the drug to a target cell due to the high antigen specificity of the parent antibody included in the conjugate, and thus can increase the therapeutic effect of the drug. Also, it can increase the utility of drugs, particularly anticancer drugs with high anticancer efficacy, the use of which is restricted due to their toxicity.

Moreover, the present invention relates to a composition, including the modified antibody-drug conjugates, for the treatment of diseases, particularly cancer and to a method of treating diseases using the modified antibody-drug conjugate.

The modified antibody-drug conjugate according to the present invention may contain a number of cysteine residues that can be used for conjugating to drugs, because the motif containing one or more cysteine residues is bound to the parent antibody. Thus, it can contain a large amount of drugs bound thereto, and the large amount of bound drug can be effectively delivered to a target cell or tissue. Moreover, because the number of cysteine residues that are bound to the parent antibody can be easily controlled, the amount of the drug contained in the modified antibody-drug conjugate (mADC) can be easily controlled to a desired level.

In addition, because the modified antibody-drug conjugate according to the present invention can accurately deliver the drug to a target cell due to its high specificity to an antigen, it can increase the therapeutic effect of the drug and can also improve the utility of drugs, particularly anticancer drugs, which are restricted in use due to their toxicity, despite their high anticancer effect.

BACKGROUND

Among biopharmaceuticals, therapeutic agents using antibody are being most actively studied, which bind specifically to targets (i.e., antigens) that are expressed specifically in certain diseases. Particularly, identification of tumor-related antigens that are expressed on the surface of cancer cells is being actively performed, and methods of diagnosing and treating tumors using antibodies (i.e., anticancer antibodies) that bind to the antigens to inhibit cell growth or induce cell death are being widely used, and the field of these methods also has a very good prospect.

Such anticancer antibodies have very high target specificity, but their cytotoxic effects on the cancer cells are usually lower than those of existing cytotoxic drugs (i.e., anticancer drugs or agents). So in many cases, these anticancer antibodies are subject to a combination therapy with cytotoxic drugs or other cell proliferation inhibitory drugs.

In connection with the combination therapy as described above, there have been active studies on a modified antibody-drug conjugate (mADC), in which the therapeutic effect of the bound-cytotoxic drugs increases while the toxicity decreases. It is recognized that when the modified antibody-drug conjugate is used, the systemic toxicity of the drug can be reduced and the cytotoxicity of the drug can be enhanced specifically in cells (particularly cancer cells) having a target overexpressed therein, thereby increasing the therapeutic effect of the drug.

Indeed, modified antibody-drug conjugates comprising a cytotoxic drug or radioisotope conjugated to an antibody, such as ZEVALIN™ [Witzig et al., J. Clin. Oncol, 2002, 20(15): 3262-3269]) or MYLOTARG™ [Drugs of the Future, 2000, 25(7):686]), have been successfully developed for the treatment of non-Hodgkin lymphoma or acute myeloid leukemia. In addition, many attempts have been made to conjugate highly toxic mertansine (such as cantuzumab mertansine (Immunogen, Inc. [Xie et al., J. of Pharm. and Exp. Ther. 2004, 308 (3):1073-1082]) or trastuzumab mertansine (Roche [Isakoff et al., J. Clin. Oncol. 2011, 29(4): 351-4])) to an antibody or conjugate other cytotoxic drugs, for example, dolastatin derivatives such as auristatin peptides, auristatin E (AE), monomethyl auristatin (MMAE) or MMAF to antibodies like cBR96 (specific to Lewis Y on carcinomas), cAC10 which is specific to CD30 on hematological malignancies, or anti-CD20 antibody for treatment of CD20-expressing cancer, or Rituxan for immune disorders, anti-EphB2R antibody for treatment of colorectal cancer, 2H9, anti-IL-8, or E-selectin antibody ([Klussman, et al., Bioconjugate Chemistry, 2004, 15(4):765-773]; [Doronina et al., Nature Biotechnology, 2003, 21(7):778-784]; [Francisco et al., Blood, 2003, 102(4):1458-1465]) US 2004/0018194 A1) WO 04/032828 A3; [Mao et al., Cancer Research, 2004, 64(3):781-788]; [Bhaskar et al., Cancer Res, 2003, 63:6387-6394]).

In addition, an attempt has also been made to develop modified antibody-drug conjugates using daunomycin, doxorubicin, methotrexate or vindesine. It is known that bacterial toxins such as diphtheria toxin, plant toxins such as ricin, or small molecules such as geldanamycin ([Mandler et al., J. of the Nat. Cancer Inst, 2000, 92 (19):1573-1581]; [Mandler et al., Bioorganic & Med. Chem. Letters, 2000, 10: 1025-1028]; [Mandler et al., Bioconjugate Chem, 2002, 13:786-791]), maytansinoid ([EP 1391213 A1]; [Liu et al., Proc. Natl. Acad. Sci. USA, 1996, 93: 8618-8623]) or calicheamicin ([Lode et al., Cancer Res, 1998, 58: 2928]; [Hinman et al., Cancer Res, 1993, 53: 3336-3342]) may be used as drugs in antibody-drug conjugates. These cytotoxic drugs exhibit cytotoxic and cell proliferation inhibitory effects by mechanisms such as tubulin binding, DNA binding or topoisomerase inhibition.

When a conventional process that was used to induce covalent linkage between a drug and an antibody is employed to prepare the antibody-drug conjugate as described above, the drug will be bound to a number of sites in the antibody, producing a heterogeneous mixture. For example, a cytotoxic drug is likely to be bound to an antibody through a number of lysine residues contained in the antibody to produce a heterogeneous antibody-drug conjugate mixture. Also, the heterogeneous mixture might have different drug binding distribution ranging from 0 to about 8 depending on reaction conditions, which means that the number of drug molecules bound per unit antibody varies.

Also for the antibody drug conjugate having the defined number of drug binding, there might be another potential heterogeneity, depending on the various conjugation sites. Homogeneous purification from this heterogeneous mixture is not suitable for use in the mass production of medicines ([Hamblett et al., Clin. Cancer Res, 2003, 10, 7063-7070], [Wang et al., Protein Sci. 2005, 14, 2436-2446]).

Another method for conjugating a drug to an antibody is reducing disulfide bonds between cysteine residues in antibody by reducing agents, and then conjugating drugs to free thiol groups of the reduced cysteine residues. This method also has disadvantages in that the inherent characteristics of the antibody can be lost and a heterogeneous mixture is produced in large amounts. Specifically, immunoglobulin M is an example of a disulfide-linked pentamer, while immunoglobulin G is an example of a protein with internal disulfide bridges bonding the subunits together. In such proteins, reduction of the disulfide bonds with a reagent such as dithiothreitol (DTT) or selenol generates reactive free thiols ([Singh et al., Anal. Biochem. 2002, 304:147-156]). This approach may result in loss of antibody tertiary structure and antigen binding specificity ([Jagath et al., Nature Biotechnology, 2008, 26(8):925-32]).

The representative disadvantage of the conventional antibody-drug conjugation method as described above is that it is difficult to precisely control the drug conjugation sites in antibody and the number of conjugated drugs. In an attempt to overcome this problem and to introduce a free thiol group, a specific amino acid was substituted with cysteine where the substituted cysteine did not impair the function of an antibody. For this purpose, a screening method for optimum cysteine mutant was developed after predicting the reactivity of thiol group in each possible mutating site in antibody (Korean Patent Laid-Open Publication No. 2007-0054682, 'ThioFab technology'). An antibody-drug conjugate of trastuzumab mertansine produced by this method is in clinical trials for treatment of metastatic breast cancer ([Burris III et al., J. Clin. Oncol, 2011, 29(4):398-405]). The above-described ThioFab technology has an advantage in that damage to a disulfide bond in a parent antibody can be minimized by introducing a new cysteine into the antibody, but the concern about modification of the structure and the function of the parent antibody still remains, because some amino acids in the parent antibody are mutated by cysteine.

Accordingly, there is an urgent need for the development of a novel antibody-drug conjugate and a production method thereof, in which the number and position of drug molecules conjugated to a parent antibody can be accurately controlled while retaining the structural and functional characteristics of the parent antibody.

DISCLOSURE OF INVENTION

The present invention has been made in order to solve the above-described problems occurring in the prior art, and it is an object of the present invention to provide a novel antibody (hereinafter referred to as "modified antibody"), which comprises a motif containing one or more cysteine residues bound to a parent antibody to provide a plurality of drug-binding sites. Another object of the present invention is to provide a modified antibody-drug conjugate comprising a drug bound to the modified antibody.

The modified antibody according to the present invention can efficiently be conjugated with various drugs while retaining the characteristics of a parent antibody, and thus it can have a high target specificity and increase the therapeutic effect of the conjugated drugs.

The modified antibody of the present invention has advantages in that it comprises a motif containing one or more cysteine residues, and thus a drug can be conjugated to the cysteine residues and the conjugated drug can be effectively delivered to a target tissue. In addition, the number of cysteine residues that can bind to the drug can be accurately controlled, and thus the number or amount of drug molecules in the modified antibody-drug conjugate can be controlled. Accordingly, the modified antibody-drug conjugate of the present invention can be used as an excellent drug delivery system that overcomes the problem of conventional antibody-drug conjugates and can be efficiently used for the treatment of diseases such as cancer.

BEST MODE FOR CARRYING OUT THE INVENTION

Figure 1:
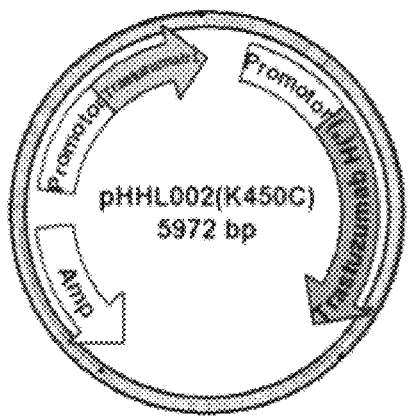
FIG. 1 is a vector map of a modified-antibody expression vector comprising cysteine-containing trastuzumab.

Hereinafter, the present invention will be described in further detail.

The present invention provides a novel modified antibody, which comprises a motif containing one or more cysteine residues bound to a parent antibody to provide a plurality of antibody drug sites, and a modified antibody-drug conjugate comprising the modified antibody. Such a modified antibody can be conjugated to various drugs while retaining the characteristics of the parent antibody, and thus can be efficiently used as a modified antibody-drug conjugate.

As used herein, the term "parent antibody" means a conventional "antibody" having no cysteine-containing motif. Any parent antibody having binding affinity and specificity to a specific antigen may be used in the present invention without limitation. Examples of parent antibodies that may be used in the present invention include monoclonal or polyclonal antibodies, such as antibodies derived from animals such as mice, chimeric antibodies, humanized antibodies, and human antibodies developed using transgenic mice or phage-display technology. In addition, it will be obvious to those skilled in the art that modified antibodies such as bispecific antibodies, or fragments of the antibodies, may also be used in the present invention.

As used herein, the term "fragment of the antibody" refers to a fragment that at least retains a binding affinity to an antigen. Examples of the antibody fragment include single-chain antibodies, diabodies, triabodies, tetrabodies, Fab fragments, F(ab')$_2$ fragments, Fd, scFv, domain antibodies, minibodies, single-chain antibodies (scAb), derivatives of antibody constant regions, and artificial antibodies based on protein scaffolds.

In addition, examples of parent antibodies that may be used in the present invention include all types of immunoglobulin molecules (e.g., IgG, IgE, IgM, IgD, and IgA) and subtypes thereof (e.g., IgG1, IgG2, IgG3, IgG4, IgA1 and IgA2). In addition, the parent antibody may be one derived from any species.

The parent antibody in the present invention has binding affinity and specificity to cancer-specific antigens such as tumor-associated antigens (TAAs), cell surface receptor proteins, cell surface proteins and molecules other than receptor, transmembrane proteins, signaling proteins, cell survival regulators, cell proliferation regulators, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis.

Specifically, antigens to which the parent antibody in the present invention can bind, but are not limited to:

(1) BMPRIB (bone morphogenetic protein receptor-type IB; Genbank Accession No. NM_001203);

(2) E16 (LAT1, SLC7A5; Genbank Accession No. NM_003486);

(3) STEAP1 (six transmembrane epithelial antigen of prostate; Genbank Accession No. NM_012449);

(4) 0772P (CA125, MUC16, Genbank Accession No. AF361486);

(5) MPF (MPF, MSLN, SMR, megakaryocyte potentiating factor, mesothelin; Genbank Accession No. NM_005823);

(6) Napi3b (NAPI-3B, NPTIIb, SLC34A2, solute carrier family 34 (sodium phosphate), member 2, type II sodium-dependent phosphate transporter 3b; Genbank Accession No. NM_006424);

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B; Genbank Accession No. AB040878);

(8) PSCA hlg (2700050C12Rik, C530008O16Rik, RIKEN cDNA 2700050C12, RIKEN cDNA 2700050C12; Genbank Accession No. AY358628);

(9) ETBR (Endothelin type B receptor; Genbank Accession No. AY275463);

(10) MSG783 (RNF124, hypothetical protein FLJ20315, Genbank Accession No. NM_017763);

(11) STEAP2 (HGNC_8639, IPCA-1, PCANAP1, STAMP1, STEAP2, STMP, prostate cancer associated gene 1, prostate cancer associated protein 1, six-transmembrane epithelial antigen of prostate 2, six-transmembrane prostate protein, Genbank Accession No. AF455138);

(12) TrpM4 (BR22450, FLJ20041, TRPM4, TRPM4B, transient receptor potential cation channel, subfamily M, member 4; Genbank Accession No. NM_017636);

(13) CRIPTO (CR, CR1, CRGF, CRIPTO, TDGF1, teratocarcinoma-derived growth factor; Genbank Accession No. NP_003203 or NM_003212);

(14) CD21 (CR2 (Complement receptor 2) or C3DR (C3d/Epstein Barr virus receptor) or Hs.73792; Genbank Accession No. M26004);

(15) CD79b (CD79B, CD79β, IGb (immunoglobulin-associated beta), B29, Genbank Accession No. NM_000626);

(16) FcRH2 (IFGP4, IRTA4, SPAP1A (SH2 domain containing phosphatase anchor protein 1a), SPAP1B, SPAP1C; Genbank Accession No. NM_030764);

(17) HER2 (Genbank Accession No. M11730);

(18) NCA (Genbank Accession No. M18728);

(19) MDP (Genbank Accession No. BC017023);

(20) IL20Rα (Genbank Accession No. AF184971);

(21) Brevican (Genbank Accession No. AF229053);

(22) EphB2R (Genbank Accession No. NM_004442);

(23) ASLG659 (Genbank Accession No. AX092328);

(24) PSCA (Genbank Accession No. AJ297436);

(25) GEDA (Genbank Accession No. AY260763);

(26) BAFF-R (B cell-activating factor receptor, BLyS receptor, BR3, NP_443177.1);

(27) CD22 (B-cell receptor CD22-B isoform; NP-001762.1);

(28) CD79a (CD79A, CD79.alpha., immunoglobulin-associated alpha, a B cell-specific protein that covalently interacts with Ig beta (CD79B) and forms a complex on the surface with IgM molecules, transduces a signal involved in B-cell differentiation; Genbank Accession No. NP_001774.1);

(29) CXCR5 (Burkitt's lymphoma receptor 1, a G protein-coupled receptor that is activated by the CXCL 13 chemokine, functions in lymphocyte migration and humoral defense, plays a role in HIV-2 infection and regarded for development of AIDS, lymphoma, myeloma, and leukemia; Genbank Accession No. NP_001707.1);

(30) HLA-DOB (Beta subunit of MHC class II molecule (Ia antigen) that binds peptides and presents them to CD4+ T lymphocytes; Genbank Accession No. NP_002111.1);

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability; Genbank Accession No. NP_002552.2);

(32) CD72 (B-cell differentiation antigen CD72, Lyb-2; Genbank Accession No. NP_001773.1);

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis; Genbank Accession No. NP_005573.1);

(34) FcRH1 (Fc receptor-like protein 1, a putative receptor for the immunoglobulin Fc domain that contains C2 type Ig-like and ITAM domains, may have a role in B-lymphocyte differentiation; Genbank Accession No. NP_443170.1);

(35) IRTA2 (Immunoglobulin superfamily receptor translocation associated 2, a putative immunoreceptor with possible roles in B cell development and lymphomagenesis; deregulation of the gene by translocation occurs in some B cell malignancies; Genbank Accession No. NP_112571.1); and

(36) TENB2 (putative transmembrane proteoglycan, related to the EGF/heregulin family of growth factors and follistatin; Genbank Accession No. AF179274). In addition, examples of the antigens include all antigens that may be used for treatment and diagnosis.

In a preferred embodiment, the parent antibody in the present invention has binding affinity and specificity to an ErbB receptor selected from among EGFR, HER2, HER3 and HER4, and other cancer antigens.

Particularly, the parent antibody that is used in the present invention comprises one or more selected from among trastuzumab (trade name: Herceptin), rituximab (trade name: Rituxan), bevacizumab (trade name: Avastin), cetuximab (trade name: Erbitux), cBR96, cAC1O, anti-CD20 antibody, anti-EphB2 antibody, anti-IL-8, E-selectin antibody, anti-MUC16 antibody, and anti-CD30 antibody, but is not limited thereto.

HER2 means a member of the epidermal growth factor receptor (EGFR) family, an important signaling cascade that is implicated in the proliferation and survival of breast cancer cells. It is known that the receptor tyrosine kinases of the EGFR family are composed of erb1, erb2/HER2, erb3 and erb4 and are involved in the regulation of the adhesion, migration and differentiation of cells in addition to cell proliferation and proliferation.

There is no ligand that binds to erb2/HER2 of the four members of the erb family, but erb2/HER2 is known as the most potent oncogene in breast cancer. If the level of HER2 is normal, it is involved in the growth and development of normal mammary tissue, but if HER2 is abnormally overexpressed or amplified, normal cell regulation will be broken so that aggressive cancer cells will be formed in mammary tissue. In other words, if HER2 is activated by oligomerization with other members of the EGFR family, it will phosphorylate many downstream molecules, which leads to activation of a variety of signaling cascades. The SOS-Ras-Raf-MEK-MAPK pathway that is involved in cell proliferation and the PI-3K/Akt pathway that inhibits cell death are representative mechanisms associated with cancer cell proliferation.

The results of preclinical and clinical trials indicate that the overexpression of HER2 is an important biomarker that appears from the initial state of cancer development and plays an important role in the growth and progression of cancer. It is known that the overexpression of HER2 appears in about 20-30% of invasive breast cancers and is also associated with poor prognosis of breast cancer with higher aggressiveness and malignancy.

According to the present invention, a motif containing one or more cysteine residues is bound to a parent antibody that has specificity to a growth factor receptor selected from the group consisting of the HER2 receptors or EGF receptors. And a conventional anticancer drug is conjugated to the motif to obtain a modified antibody-drug conjugate of the present invention. When the modified antibody-drug conjugate is administered to a patient in an amount effective to inhibit the growth of tumor cells in the patient, it can exhibit an excellent effect of treating cancer by inhibiting the growth of tumor cells that overexpress the growth factor receptor while inducing the dell death.

In addition, the parent antibody in the present invention is preferably trastuzumab. Although trastuzumab is prepared so as to be substantially free of C-terminal lysine (Lys), the modified antibody-drug conjugate of the present invention could be applied to trastuzumab that contains lysine (Lys) or trastuzumab that does not contain lysine (Lys) in the C-terminal region thereof, where the cysteine (Cys)-containing motif may be bound thereto.

Amino acids in the present invention are expressed by their known 3-letter or 1-letter abbreviations. Nucleotides present in various nucleic acid fragments are designated by the standard single-letter designation used routinely in the art.

The cysteine-containing motif in the present invention has 1-100 amino acid residues, preferably 1-50 amino acid residues, more preferably 1-30 amino acid residues, and most preferably 1-10 amino acid residues, and contains one or more cysteine residues. Particularly, the cysteine-containing motif in the present invention preferably contains 1-20 cysteine residues, more preferably 1-10 cysteine residues, and even more preferably 1-5 cysteine residues.

The cysteine-containing motif in the present invention may be a simple peptide motif having no specific functionality or secondary or tertiary structure and is preferably a motif having a specific functionality or a secondary or tertiary structure. The specific functionality is preferably the property capable of maintaining/protecting the chemical conjugation ability of cysteine residues, but is not limited thereto. Particularly, the cysteine-containing motif can more effectively maintain the functionality of cysteine residues by preventing or retarding the oxidation of the cysteine residues due to binding to a specific ligand or the secondary or tertiary structure of the peptide motif itself.

The cysteine-containing motif in the present invention has a structure represented by the following formula 1:

$$Xa\text{-}[(M_{Cys})_n\text{-}Xb_n]_n \qquad \text{Formula (1)}$$

wherein $(M_{Cys})_n$ represents a simple cysteine residue or a peptide motif that contains a cysteine residue and has a specific functionality or a secondary or tertiary structure; Xa and $Xb_n$ each independently represents a peptide comprising 0 to 20 amino acid residues other than cysteine; and n is an integer ranging from 1 to 20.

In formula (1), $(M_{Cys})_n$, that is, $(M_{Cys})_1$, $(M_{Cys})_2$ .... $(M_{Cys})_n$, may be the same as or different from each other. Also, $Xb_n$, that is, $Xb_1$, $Xb_2$ .... $Xb_n$, may be the same as or different from each other.

In addition, if $(M_{Cys})_n$ in formula (1) is a simple cysteine residue, the cysteine-containing motif according to the present invention has a structure represented by the following formula (2):

$$Xa\text{-}(Cys\text{-}Xb_n)_n \qquad \text{Formula (2)}$$

wherein Xa, $Xb_n$ and n are the same as defined in formula 1.

Also, if $(M_{Cys})_n$ in formula (1) is a peptide motif that contains a cysteine residue and has a specific functionality or a secondary or tertiary structure, $(M_{Cys})_n$ may preferably be a metal ion binding motif containing a cysteine residue. It is known that the metal ion binding motif containing a cysteine residue can bind to a metal ion to inhibit oxidation of the cysteine residue, thereby effectively retaining the alkylation reactivity of the cysteine residue (Van Horn et al. (2003) J. Biol. Inorg. Chem. 8: 601-610).

Examples of a metal ion binding motif containing a cysteine residue, which may be used in the present invention, include, but are not limited to, metal ion chelators (Zhang et al. (2012) Biochem. Genet. 50(7-8): 585-599) that are used to control the concentration of metal ions in vivo, chaperones (Ansbacher and Shurki, J. Phys. Chem. B (2012) 116(15): 4425-4432; Allen et al. (2012) Biochemistry 51(7): 1439-48; Click et al. (2012) H. Comput. Chem. 33(11): 1142-51) that function to deliver metal ions to a specific position outside or inside cells, transcriptional regulators (Gunther et al. (2012) Biochim. Biophys. Acta. 1823(2): 476-483; Sitthisak et al. (2012) FEMS Microbiol. Lett. 327(2): 126-133) that regulate transcription depending on the concentration of metal ions, zinc finger motifs (MacPherson et al. (2006) Microbiol. Mol. Bio. Rev. 70(3): 583-604; Schaeffer et al. (2012) Nucleic Acids Res. 40(18): 9298-9307) that are widely present in many proteins and are involved in protein-protein interactions or protein-DNA interactions, and motifs (Zielazinski et al. (2012) Biochemistry 51(40):7891-7900; Zhou et al. (2012) FEBS J. 279(2): 285-298; Cochran et al. (2011) Nat. Struct. Mol. Biol. 19(1):122-127) derived from various enzymes. The metal ion binding motifs contains a cysteine residue as an essential binding group thereof, and such metal ion binding motifs may be used in the production of the modified antibody-drug conjugate of the present invention.

Preferred examples of the metal ion binding motif in the present invention include, but are not limited to, $C_2H_2$ group ($Cys_2His_2$ class: $Cys-X_{2-4}-Cys-X_{12}-His-X_{3-5}-His$) (SEQ ID NO: 103), $C_4$ group ($C_4$ class: $Cys-X_2-Cys-X_n-Cys-X_2-Cys-X_m-Cys-X_2-Cys-X_n-Cys-X_2-Cys$) (SEQ ID NO: 104) or $C_6$ group ($C_6$ class: $Cys-X_2-Cys-X_6-Cys-X_{5-12}-Cys-X_2-Cys-X_{6-8}-Cys$) (SEQ ID NO: 105) of zinc finger protein, a $Cys-X_m-Cys$ motif such as Cys-X-X-Cys (SEQ ID NO: 106) or Cys-X-Cys, a Met-X-Cys-X-X-Cys (SEQ ID NO: 107) motif or a C-Q-C-Q-C-A-C(SEQ ID NO: 108) motif, which is frequently found in transcription regulatory proteins, metal chaperone proteins, metal ion transporters, superoxide dismutase or the like, a Ser-Pro-Cys motif of membrane protein ATPase, etc. In the metal binding peptide motif described above, X represents amino acid residues other than Cys; m is an integer ranging from 1 to 10, and preferably from 1 to 5; and $X_m$ or $X_{m-q}$ represents amino acid residues other than Cys, the number of which is indicated by m or m to q.

More specifically, examples of the metal ion binding motif of zinc finger protein, which can be used in the present invention, include, but are not limited to,

```
                                        (SEQ ID NO: 1)
       YKCKQCGKAFGCPSNLRRHGRTH, (SEQ ID NO: 2)
       YQCNICGGKCFSCNSNLHRHQRTH, (SEQ ID NO: 3)
       YSCGICGKSFSDSSAKRRHCILH, (SEQ ID NO: 4)
       YTCSDCGKAFRDKSCLNRHRRTH, (SEQ ID NO: 5)
       YRCKYCDRSFSDSSNLQRHVRNIH, (SEQ ID NO: 6)
       YKCKECGKAFNHSSNFNKHHRIH, (SEQ ID NO: 7)
       FKCPVCGKAFRHSSSLVRHQRTH, (SEQ ID NO: 8)
       YRCKYCCDRSFSISSNLQRHVRNIH, (SEQ ID NO: 9)
       YECDHCGKAFSIGSNLNVHRRIH, (SEQ ID NO: 10)
       YGCHLCCKAFSKSSNLRRHEMIH, (SEQ ID NO: 11)
       YKCKECGQAFRQRAHLIRHHKLH, (SEQ ID NO: 12)
       YKCHQCGKAFIQSFNLRRHERTH, (SEQ ID NO: 13)
       FQCNQCGASFTQKGNLNRHIKLH, (SEQ ID NO: 14)
       YTCSYCGKSFTQSNTLKQHTRIH, (SEQ ID NO: 15)
       YACHLCGKAFTQSSHRRHEKTH, (SEQ ID NO: 16)
       YKCGQCGKFYSQVSHLTRHQKIH, (SEQ ID NO: 17)
       YACHLCGKAFTQCSHLRRHEKTH, (SEQ ID NO: 18)
       YACHLCAKAFIQCSHLRRHEKTH, (SEQ ID NO: 19)
       YVCRECGRGFRQHSHLVRHKRTH, (SEQ ID NO: 20)
       YKCEECEGKAFRQSSHLTTHKIIH, (SEQ ID NO: 21)
       YECDHCGKSFSQSSHLNVHKRTH, (SEQ ID NO: 22)
       YMCSECGRGFSQKSNLTIHQRTH, (SEQ ID NO: 23)
       YKCEECGKAFTQSSNLTKHKKIH, (SEQ ID NO: 24)
       FECKDCGKAFIQKSNLIRHQRTH, (SEQ ID NO: 25)
       YVCRECRRGFSQKSNLIRHQRTH, (SEQ ID NO: 26)
       YECEKCGKAFNQSSNLTRHKKSH, (SEQ ID NO: 27)
       YECVQCGKSYSQSSNLFRHQRRH, (SEQ ID NO: 28)
       YECVQCGKGFTQSSNLITHQRVH, (SEQ ID NO: 29)
       YECNTCRKTFSQKSNLIVHQRTH,
```

-continued

YVCSKCGKAFTQSSNLTVHQKIH, (SEQ ID NO: 30)

YKCDECGKNFTQSSNLIVHKRIH, (SEQ ID NO: 31)

YECDVCGKTFTQKSNLGVHQRTH, (SEQ ID NO: 32)

YKCPDCGKSFSQSSSLIRHQRTH, (SEQ ID NO: 33)

YECQDCGRAFNQNSSLGRHKRTH, (SEQ ID NO: 34)

YECNECGKFFSQSSSLIRHRRSH, (SEQ ID NO: 35)

YKCEECGKAFNQSSTLTRHKIVH, (SEQ ID NO: 36)

YECNECGKAFAQNSTLRVHQRIH, (SEQ ID NO: 37)

YEVHDCGKSFRQSTHTLTQHRRIH, (SEQ ID NO: 38)

YECHDCGKSFRQSTHLTRHRRIH, (SEQ ID NO: 39)

HKCLECGKCFSQNTHLTRHQRTH, (SEQ ID NO: 40)

YVCDVEGCTWKFARSDELNRHKKRH, (SEQ ID NO: 41)

YHCDWDGCGWKFARSDELTRHYRKH, (SEQ ID NO: 42)

YRCSWEGCEWRFARSDELTRHFRKH, (SEQ ID NO: 43)

FSCSWKGCERRFARSDELSRHRRTH, (SEQ ID NO: 44)

FACSWQDCNKKFARSDELARHYRTH, (SEQ ID NO: 45)

YHCNWDGCGWKFARSDELTRHYRKH, (SEQ ID NO: 46)

FLCQYCAQRFGRKDHLTRHMKHSH, (SEQ ID NO: 47)

CRCNECGKSFSRRDHLVRHQRTH, (SEQ ID NO: 48)

FQCKTCQRKFSRSDHLKTHTRTH, (SEQ ID NO: 49)

FACEVCGVRFTRNDKLKIHMRKH, (SEQ ID NO: 50)

YVCDVEGCTWKFARSDKLNRHKKRH, (SEQ ID NO: 51)

YKCMECGKAFNRRSHLTRHQRIH, (SEQ ID NO: 52)

YICRKCGRGFSRKSNLIRHQRTH, (SEQ ID NO: 53)

YECKECGKAFSSGSNFTRHQRIH, (SEQ ID NO: 54)

FHCGYCEKSFSVKDYLTKHIRTH, (SEQ ID NO: 55)

YECDHCGKAFSVSSNLNVHRRIH, (SEQ ID NO: 56)

-continued

YTCKQCGKAFSVSSSLRRHETTH, (SEQ ID NO: 57)

YECNYCGKTFSVSSTLIRHQRIH, (SEQ ID NO: 58)

YRCEECGKAFRWPSNLTRHKRIH, (SEQ ID NO: 59)

FACDICGRKFARSDERKRHTKIH, (SEQ ID NO: 60)

CPVESCDRRFSRSDELTRHIRIH, (SEQ ID NO: 61)

CDICGRKFARSDERKRHTKIH, etc. (SEQ ID NO: 62)

The metal ion binding motif of zinc finger protein may be any one selected from the metal ion binding motifs of zinc finger proteins described in www.zincfingers.org, www.genenames.org/genefamilies/ZF, www.scripps.edu/mb/barbas/zfdesign/zfdesignhome.php, zifdb.msi.umn.edu:8444/ZiFDB/, or Macpherson et al. (2006) Microbiol. Mol. Biol. Rev. 70(3), 583-604, which is consistent with the technical characteristics of the present invention.

Examples of the metal ion binding motif of transcription regulatory proteins, metal chaperone proteins or the like, which can be used in the present invention, include, but are not limited to, the followings:

CadC protein:
CEIFCYDEEKVNRIQGDLQTVDISGVSQILKAIADENRAKITYALC (SEQ ID NO: 63)
QDEELCVC, AztR protein:
DTHLVHLDNVRSSQAQILPTDKAQQMAEIFGVLADTNRIRLLSALA (SEQ ID NO: 64)
SSELCVC, ZiaR protein:
CDQPLVHLEQVRQVQPEVMSLDQAQQMAEFFSALADPSRLRLMSAL (SEQ ID NO: 65)
ARQELCVC, BxmR protein:
CDRAHLVDCSRVGDIQTQVLNTAKAQRMAEFFSLLGDANRLRVVSV (SEQ ID NO: 66)
LAKQELCVC, ArsR protein:
LSDETRLGIVLLLREMGELCVCDLCM, (SEQ ID NO: 67)

CCTLATGPLSSDESEHYADLFKVLGDPVRLRILSQLAAGGC, (SEQ ID NO: 68)

YRAAMPVVRALVAYLTENCCHGTRDC, (SEQ ID NO: 69)

CmtR protein:
CLRGCGLVVATYEGRQVRYALADSHLARALGELVQVVLAVDTDQPC, (SEQ ID NO: 70)

LRDCGLVVTVPDGRRSRYELADERLGHALDDLRAAVVAVDADRTCP (SEQ ID NO: 71)
DADELECC, etc.

Zinc (Zn) binding proteins found in membrane proteins that are involved in bacterial signaling transduction have an inherent metal ion binding motif composed of one cysteine residue and three histidine residues (Draper et al., J. Bacteriol. 2011, 193 (17), 4338-4345). Herein, the metal ion binding motif has a structure of HXXWFYLX$_{21-28}$CXLF-MVIGXWFLVIX$_{18-27}$HXXH (SEQ ID NO: 109), wherein X represents any amino acid, and X$_{m-q}$ represents amino acid residues other than Cys, the number of which is indicated by m to q. In addition, 150 or more zinc binding proteins reported to date may be used as the metal ion binding motif in the present invention.

Known metal ion transporters include cation diffusion facilitators, Zrt, Irk-like proteins, cation exchangers, copper transporters, heavy metal P-type ATPase, ATP-binding cassette transporters, etc. (Hanikenne et al. Plant Physiology 2005, 137, 428-446; Hall and Williams, J. Experimental Botany, 2003, 54(393) 2601-2613), and the following M-X-C-X-X-C (SEQ ID NO: 110) motif may preferably be used in the present invention, but is not limited thereto:

```
E.coli ZntA:
                                    (SEQ ID NO: 72)
VSGMDCAACARKVENAVRQLAGVNQVQVLFA Tn501 MerP:
                                    (SEQ ID NO: 73)
VPGMTCSACPITVKKAISEVEGVSKVDVTFE Tn501 MerA:
                                    (SEQ ID NO: 74)
ITGMTCDSCAAHVKEALEKVPGVQSALVSY S.aureus CadA:
                                    (SEQ ID NO: 75)
VQGFTCANCAGKFEKNVKKIPGVQDAKVNFG Human Menkes:
                                    (SEQ ID NO: 76)
VEGMTCNSCVWTIEQQIGKVNGEHHIKVSLE Yeast Atx1:
                                    (SEQ ID NO: 77)
VVMTCSGCSGAVNKVLTKLEPDVSKIDIS Rat Wilsons:
                                    (SEQ ID NO: 78)
GMTCASCVANIERNLRREEGIYSV Hum Wilsons:
                                    (SEQ ID NO: 79)
YEGMTCQSCVSSIEGKYRKLQGVVRYKVSL Rice Cu ATPase:
                                    (SEQ ID NO: 80)
GMSCQGCAGAVRRVLTKMEGVETFDIDME H.pylori Cu ATPase:
                                    (SEQ ID NO: 81)
VPSITCSHCVDKIEKFVGEIEGVSFIDANVE Ran1:
                                    (SEQ ID NO: 82)
VTGMTCAACSNSVEAALMNVNGVDVGGMTCG
GCSASVKKLLESQPCVASASV Cpx89:
                                    (SEQ ID NO: 83)
VSGMVCAACSTAVENALLSCSGV Paa1:
                                    (SEQ ID NO: 84)
DVGGMTCGGCSASVKKILESQP Cpx1184:
                                    (SEQ ID NO: 85)
DVGGMKCGGCVEHVKKILEEQFGVTSAS
```

In addition, various metal ion binding motifs artificially designed based on wild-type metal ion binding motifs found in vivo may be used in the modified antibody-drug conjugate according to the present invention. Examples for these metal binding motifs include, but are not limited to, a CGH motif (Van Horn et al. (2003) J. Biol. Inorg. Chem. 8: 601-610) designed based on a GGH motif from Zinc finger protein which does not contain cysteine residue and metal ion binding motifs (Jancso et al. (2011) Metallomics 3(12): 1331-1339) obtained by substituting one or more cysteine residues in a peptide motif with other amino acid residue such as threonine, serine or histidine. The CGH motif has a structure represented by the following chemical formula 1, and preferably has a structure of ACGHA (SEQ ID NO: 111) having alanines both at the C- and the N-termini.

Chemical Formula 1

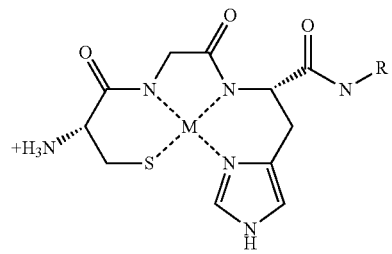

[wherein M represents a metal ion, and R represent an amino acid residue other than cysteine, preferably alanine.]

The CGH motif in the present invention still has the metal ion binding property even when the positions of the N-terminus and the C-terminus are reversed. Thus, it will be obvious to those skilled in this field of art that an HGC motif having the reversed positions of the N-terminus and the C-terminus falls within the scope of the CGH motif in the present invention.

Metal ion binding motifs artificially designed based on zinc finger motifs, which may be used in the present invention, include the following metal binding peptide motifs (see Roehm and Berg, J. Am. Chem. Soc. 1998, 120. 13083-13087) obtained by substituting a cysteine residue (which plays the most essential role) in PYKCPECGKSFSQKSALVKHQRTHTH (SEQ ID NO: 89) with methylcysteine (Me-Cys) or substituting a histidine residue in this sequence with cysteine:

```
                                    (SEQ ID NO: 86)
PYKCPECGKSFSQKSALVKHQRTHTC, (SEQ ID NO: 87)
PYKCPECGKSFSQKSALVKHQRTHTM, (SEQ ID NO: 88)
PYKCPECGKSFSQKSALVKHQRTHT(Me-C), (SEQ ID NO: 89)
PYK(Me-C)PECGKSFSQKSALVKHQRTHTH, (SEQ ID NO: 90)
PYKCPE(Me-C)GKSFSQKSALVKHQRTHTH,
and
                                    (SEQ ID NO: 91)
PYKCPE(Me-C)GKSFSQKSALVKHQR.
```

[In the metal binding peptide motif described above, Me-C represents a methylated cysteine residue.]

In addition, peptides artificially designed based on many metal ion binding protein motifs reported to date may also be used in the present invention.

Metal ion binding motifs based on the secondary or tertiary structure of protein include beta-sheets, mixed alpha/beta motifs, and alpha-helix structures which are most frequently found. The alpha-helix structures include peptides having single-stranded, double-stranded, triple stranded or quadruple-stranded alpha-helix structures.

With respect to these multiple-stranded alpha-helices, the TRI family, for example, has a structure of G(LKALEEK)₄G having four repeats of the peptide sequence LKALEEK (residues 2-8 of SEQ ID NO: 92). Artificially designed metal ion-binding peptide motifs obtained by substituting a specific amino acid in this TRI family with cysteine have been reported (Peakcock et al. 2009. Dalton Trans. 7(13). 2271-2280), and artificially designed peptide motifs having the following structures may be used in the present invention, but are not limited thereto:

GLKALEEKCKALEEKLKALEEKLKALEEKG (SEQ ID NO: 92)

GLKALEEKLKALEEKLKACEEKLKALEEKG (SEQ ID NO: 93)

GLKALEEKCKALEEKLKACEEKLKALEEKG (SEQ ID NO: 94)

GLKALEEKLKALEEKCKALEEKLKALEEKG (SEQ ID NO: 95)

GLKALEEKLKALEEKLKALEEKCKALEEKG (SEQ ID NO: 96)

GLKALEEKLKALEEKLKALEEKLKAAEEKCKALEEKG (SEQ ID NO: 97)

GLKALEEKLKALEEKCKALEEKLKAAEEKCKALEEKG (SEQ ID NO: 98)

ELYALEKELGALEKELACLEKELGALEKELYALEK (SEQ ID NO: 99)

KLYALKEKLGALKEKLACLKEKLGALKEKLYALKE (SEQ ID NO: 100)

ELYALEKELGALEKELACLKEKLGALKEKLYALKE (SEQ ID NO: 101)

KLYALKEKLGALKEKLACLEKELGALEKELYALEK. (SEQ ID NO: 102)

In addition, many metal ion binding peptide motifs (Nivorozhkin et al. 2000. Inorg. Chem. 39(11) 2306-2313) having a circular structure, such as Cyclo[K 1,12] (QCGVCGKCIACK) (SEQ ID NO: 112), may also be used in the present invention.

Cysteine-containing metal ion binding motifs that may be used in the modified antibody of the present invention are summarized in Table 1 below.

TABLE 1

Cysteine-containing metal ion binding motif structures that may be used in the present invention

| | | | Motif structures |
|---|---|---|---|
| Natural protein-derived metal ion motif | Zinc finger | $C_2H_2$ group | $Cys-X_{2-4}-Cys-X_{12}-His-X_{3-5}-His$ (SEQ ID NO: 103) |
| | | $C_4$ group | $Cys-X_2-Cys-X_n-Cys-X_2-Cys-X_n-Cys-X_2-Cys-X_n-Cys-X_2-Cys$ (SEQ ID NO: 104) |
| | | $C_6$ group | $Cys-X_2-Cys-X_6-Cys-X_{5-12}-Cys-X_2-Cys-X_{6-8}-Cys$ (SEQ ID NO: 105) |
| | transcription regulatory proteins, metal chaperone proteins | | $Cys-X_n-Cys$ |
| | membrane proteins | | $HXXWFYLX_{21-28}$ $CXLFMVIGXWFLVIX_{18-27}HXXH$ (x is any amino acid) (SEQ ID NO: 109) |
| | metal ion transporters | | M-X-C-X-X-C (SEQ ID NO: 110) |
| Artificially synthesized metal ion motif | zinc finger motif | | PYKCPECGKSFSQKSALVKHQRTHTH modified peptide (SEQ ID NO: 113) ACGHA (SEQ ID NO: 111) |
| | mutiple-stranded-helices | TRI family | Modified peptide of $(LKALEEK)_n$ (n = 1 to 5) (SEQ ID NO: 114) |
| | | Others | Cyclo (K 1,12)-QCGVCGKCIACK ELYALEKELGALEKELACLEKELGALE KELYALEK (SEQ ID NO: 115) |

Such cysteine-containing motifs may be bound to the N-terminus or C-terminus of the light or heavy chain of a parent antibody without limitation, so long as a target drug can be conjugated thereto while maintaining the specificity of the parent antibody. The motif is preferably bound to the C-terminus of the heavy or light chain. Particularly, it is bound to the C-terminus of the heavy chain, that is, the terminus of the constant region of the parent antibody. If an antibody fragment is used, the motif is preferably bound to the C-terminus of the heavy chain of the fragment.

However, as long as the specificity of the parent antibody is maintained, the cysteine-containing motif in the present invention, specifically cysteine motif having a metal ion-binding functionality or certain specific functionality or a secondary or tertiary structure, could be linked to any position other than the heavy and light chain of the parent antibody and may be introduced into the parent antibody by a long-chain peptide linker. It is well known that, when an antibody-drug conjugate is produced by conjugating drugs to site-specifically mutated cysteine or lysine residues in either heavy or light chains (except CDR region) of antibody through a long-chain hydrocarbon linker, it still can retain the structural characteristics and specificity of the parent antibody. Thus, a cysteine-containing metal ion binding peptide motif linked to this position of the parent antibody by a long-chain peptide linker can provide an antibody-drug conjugate that has high homogeneity while retaining the specificity of the parent antibody.

In the modified antibody according to the present invention, the cysteine-containing motif can be fused directly to the parent antibody by an amide bond. Alternatively, the terminal functional group of the cysteine-containing motif can be chemically bound to the terminal functional group of the parent antibody. Alternatively, the motif can also be bound to the parent antibody in a linker mediated manner by using a first linker.

A drug can be conjugated directly to the cysteine residue and the thiol group (—SH) of the cysteine in the cysteine-containing motif bound to the parent antibody and may also be linked to the cysteine residue through a second linker.

Binding of the second linker that links a drug to the cysteine residue in the cysteine-containing motif may be performed by using alkylation, disulfide exchange or trans-thioesterification. The second linker may be one or more selected from among alkyl halide derivatives containing a haloacetyl functional group, derivatives containing a maleimide group, aziridine derivatives, acryloyl derivatives, and aryl halide derivatives containing fluorobenzene or the like, but is not limited thereto. The derivatives may be bound to the thiol group of the cysteine residue in the motif by an alkylating reactive group, an arylating reactive group, a maleimide group, an aziridine group, an acryloyl group, or a disulfide exchange reactive group containing pyridyl disulfide and thionitrobenzoic acid (Bioconjugate techniques, 2nd edition, pp 182~192, Gerg T. Hermanson, ELSVIER).

For example, a maleimide group that is generally used for linking thiol and a linker is used to conjugate a drug to cysteine, because the nucleophilic reactivity of the thiol group of a cysteine residue for the maleimide group is about 1000 times higher than that of the amine group or N-terminal amine group of other amino acid residue, such as lysine residues. Thus in the case of a modified antibody-drug conjugate comprising maleimide or iodoacetamide as the second linker, cysteine is bound to the drug by a thioether bond. Generally, the second linker has a reactive site having an electrophilic group that reacts with nucleophilic cysteine present on the antibody.

A drug that is bound to the modified antibody of the present invention may be any drug having disease therapeutic effects. Particularly, it is preferably a cancer therapeutic drug having the effect of inhibiting the proliferation of tumor cells.

Specifically, a drug that may be used in the modified antibody-drug conjugate of the present invention comprises any compound, moiety or group that has the effect of cytotoxicity or inhibiting cell proliferation, and examples thereof include:

(i) chemotherapeutic agents capable of functioning as microtubulin inhibitors, mitotic inhibitors, topoisomerase inhibitors, or DNA intercalators;

(ii) protein toxins capable of functioning as enzymes;

(iii) micro-RNA (miRNA), siRNA, or shRNA, which can inhibit the expression of a specific oncogene; and (iv) radioisotopes.

Examples of such drugs include, but are not limited to, maytansinoid, auristatin, dolastatin, trichothecene, CC1065 (cytotoxic compound), calicheamicin and other enediyne antibiotics, taxane, anthracycline, methotrexate, adriamycin, vindesine, vinca alkaloids (vincristine, vinblastine, etoposide), doxorubicin, melphalan, mitomycin C, chlorambucil, daunorubicin, daunomycin, and stereoisomers, isosteres, analogs or derivatives thereof, other intercalating agents, enzymes and fragments thereof such as nucleolytic enzymes, antibiotics, and toxins such as small molecule toxins or enzymatically active toxins of bacterial, fungal, plant or animal origin, and various antitumor or anticancer agents such as cisplatin, CPT-11, doxorubicin, paclitaxel and docetaxel.

In addition, a nucleophilic group on the drug moiety in the present invention includes one or more selected from amine, thiol, hydroxyl, hydrazide, oxime, hydrazine, thiosemicarbazone, hydrazine carboxylate and aryl hydrazide groups, which can react with the second linker moiety and an electrophilic group on the second linker reagent to form a covalent bond, but is not limited thereto.

As described above, the number of drug molecules that can be conjugated to the antibody by the second linker moiety can increase as the number of cysteine residues in the motif bound to the parent antibody increases.

As described above, the modified antibody according to the present invention can comprise a number of cysteine residues, because the motif containing one or more cysteine residues is bound to the parent antibody, preferably the C-terminus of the parent antibody. Thus, a large amount of a drug can be conjugated to the modified antibody in the present invention, and a large amount of the conjugated drug can be effectively delivered to a target cell or tissue.

Also, because the number of cysteine residues that are bound to the parent antibody is easily controlled, the amount of a drug that is contained in the modified antibody-drug conjugate (mADC) can be easily controlled to a desired level. This characteristic feature overcomes the shortcomings of conventional modified antibody-drug conjugates, and the novel modified antibody-drug conjugate according to the present invention can be used as an excellent drug delivery system and can be used efficiently for the treatment of diseases such as cancer.

The present invention also provides a method for producing a modified antibody, which comprises a motif containing one or more cysteine residues bound to a parent antibody.

The parent antibody can be produced by constructing a suitable expression vector containing a nucleotide sequence encoding the heavy-chain or light-chain constant domain of the parent antibody, transforming a prokaryotic or eukaryotic cell with the constructed expression vector to express an antibody protein, isolating the antibody protein, and then purifying the isolated antibody protein to a pharmaceutically acceptable purity.

A suitable expression vector in the present invention may include expression regulatory elements, such as a promoter, an initiation codon, a stop codon, a polyadenylation signal, and an enhancer, as well as signal sequences for membrane targeting or secretion. Examples of promoters that are generally available in prokaryotic cells include lac, tac, T3 and T7 promoters. Examples of promoters available in eukaryotic cells include simian virus 40 (SV40) promoter, mouse mammary tumor virus (MMTV) promoter, human immunodeficiency virus (HIV) promoter such as the HIV Long Terminal Repeat (LTR) promoter, moloney virus promoter, cytomegalovirus (CMV) promoter, epstein barr virus (EBV) promoter, rous sarcoma virus (RSV) promoter, as well as β-actin promoter, promoters from human genes such as human, human hemoglobin, human muscle creatine and human metallothionein.

An expression vector may include a selectable marker that allows selection of host cells containing the vector. Markers that confer selectable phenotypes, such as resistance to drugs, nutrient requirement, resistance to cytotoxic agents or expression of surface proteins, are used as selectable markers. Since only cells expressing a selectable marker survive in the environment treated with a selective agent, transformed cells can be selected. Also, a replicable expression vector may include a replication origin with a specific nucleic acid sequence which initiates replication.

As recombinant expression vectors for expressing exogeneous genes, various types of vectors such as plasmid, virus or cosmid vectors may be used. The type of recombinant vector is not specifically limited, as long as it functions to express a desired gene in various host cells such as prokaryotic and eukaryotic cells and to produce a desired protein. However, it is preferable to use a vector that includes a promoter exhibiting strong activity and can produce exogeneous protein, which retains similarity to a naturally occurring protein, with high yield.

A variety of expression host/vector combinations may be used to express a parent antibody or a modified antibody comprising a motif containing one or more cysteine residues. Useful expression vectors for eukaryotic hosts include, but are not limited to, vectors comprising expression control sequences from SV40, bovine papilloma virus, adenovirus, adeno-associated virus, cytomegalovirus and retrovirus. Useful expression vectors for bacterial hosts include bacterial plasmids, such as plasmids from E. coli, including pET, pRSET, pBluescript, pGEX2T, pUC, col E1, pCR1, pBR322, pMB9 and their derivatives, wider host range plasmids, such as RP4, phage DNAs, e.g., the numerous derivatives of phage lambda, e.g. λgt10, λgt11, NM989, and other DNA phages, such as M13 and filamentous single stranded DNA phages. Useful expression vectors for yeast cells include the 2 μm plasmid and derivatives thereof. Useful vectors for insect cells include pVL 941.

In another aspect, the present invention provides a host cell transformed with the above-described recombinant vector. The recombinant vector is inserted into a host cell to form a transformant. A suitable host cell to be transformed with the vector may be a prokaryotic cell such as E. coli, Bacillus subtilis, Streptomyces sp., Pseudomonas sp., Proteus mirabilis or Staphylococcus sp. Also, the host cells may be fungal cells such as Aspergillus sp., yeast cells such as Pichia pastoris, Saccharomyces cerevisiae, Schizosaccharomyces sp. and Neurospora crassa, lower eukaryotic cells, and higher eukaryotic cells such as insect cells. Also, the host cells may be derived from plants and/or mammals. Preferred examples of the host cells include, but are not limited to, PER.C6 cells, monkey kidney cells 7 (COS7; particularly simian COS cells), NSO cells, SP2/0, Chinese hamster ovary (CHO) cells, W138, baby hamster kidney (BHK) cells, Madin-Darby canine kidney (MDCK) cells, myeloma cell lines, HuT 78 cells, HEK293 cells, and other mammalian host cells that produces the antibody protein according to the present invention.

Particularly, to maximize expression efficiency, the host cell in the present invention is preferably one or more selected from among E. coli cells, simian COS cells, Chinese hamster ovary (CHO) cells, and other mammalian host cells that produces the antibody protein according to the present invention. More preferably, the host cell in the present invention is the hamster ovary cell CHO-K1.

In the present invention, "transformation" into host cells include any method for introducing nucleic acids into organisms, cells, tissues, or organs and may be performed using a standard technique selected depending on the type of host cell as known in the art. Examples of this method include, but are not limited to, electroporation, protoplast fusion, calcium phosphate ($CaPO_4$) precipitation, calcium chloride ($CaCl_2$) precipitation, agitation using silicon carbide fiber, agrobacterium-mediated transformation, and PEG-, dextran sulfate-, lipofectamine- or desiccation/inhibition-mediated transformation.

The antibody protein expressed as described above can be recovered from the host cell, the supernatant of the culture, or the cells after lysis, and purified by using a conventional protein purification technique, to yield the modified antibody comprising a motif containing one or more cysteine residues.

The antibody can be isolated from the culture medium by a conventional immunoglobulin purification procedure, for example, protein A Sepharose, hydroxyl-apatite chromatography, gel electrophoresis, dialysis, or affinity chromatography.

Nucleotide sequence encoding the cysteine containing motif can be fused to a nucleotide sequence encoding either heavy-chain constant domain or light-chain constant domain of parent antibody. Recombinant vector fused in this way can produce modified antibody with the similar method employed in parent antibody after transformed and expressed in prokaryotic or eukaryotic host cell.

In addition, the modified antibody of the present invention can be produced by expressing each of a parent antibody and a motif containing one or more cysteine residues, and then chemically linking the terminal functional group of the parent antibody to the terminal functional group of the cysteine-containing motif or linking the parent antibody to the motif by a first linker. A drug may be bound to the produced modified antibody with the cysteine-containing motif, thereby producing a modified antibody-drug conjugate (mADC).

Specifically, a modified antibody-drug conjugate with multiple cysteines-containing motif can be produced by:

(a) conjugating a parent antibody containing a cysteine-containing motif with a linker reagent to form an covalently bound antibody-second linker intermediate, and then add an activated drug moiety to the intermediate; or (b) conjugating the nucleophilic group of a drug moiety with a second linker reagent to form a covalently bound drug-second linker intermediate, and then add a modified antibody with a cysteine-containing motif.

In another aspect, the present invention provides a therapeutic composition comprising the modified antibody-drug conjugate as an active ingredient.

In the above mentioned composition, the drug conjugated to a modified antibody-drug conjugate may be a cytotoxic agent, a cell proliferation inhibitor, a chemotherapeutic agent, an immune inhibitor, an anti-inflammatory agent or the like, but is not limited thereto. In cancer therapy, the use of the antibody-drug conjugate for local delivery of a drug that kills or inhibits tumor cells allows the targeted delivery of the drug moiety into tumor cells by antibody-antigen interactions and the intracellular accumulation of the drug moiety. Administration of non-conjugated drug formulation may cause an unacceptable level of toxicity not only in tumor cells, but also in normal cells. However, the modified antibody-drug conjugate according to the present invention can accurately deliver the drug due to the high antigen specificity of the antibody, increasing the therapeutic effect of the drug. In addition, it can expand the usability of drugs, particularly anticancer agents, the use of which is limited due to their toxicity, despite their high anticancer efficacy. According to the present invention, an antibody-drug conjugate that maximizes drug efficacy while minimizing drug toxicity is provided.

The present invention also provides a method of inhibiting the proliferation of target cells from cancer, autoimmune, inflammatory or infectious disease by the modified antibody-drug conjugate as an active ingredient.

Cancer that can be treated according to the present invention may be one or more selected from among liver cancer, stomach cancer, breast cancer, colon cancer, bone cancer, pancreatic cancer, head and neck cancer, uterine cancer, ovarian cancer, rectal cancer, esophageal cancer, small intestine cancer, anal cancer, fallopian tube cancer, endometrial cancer, cervical cancer, vaginal cancer, valve cancer, Hodgkin's disease, prostate cancer, bladder cancer, kidney cancer, ureter cancer, renal cell carcinoma, renal pelvis cancer, and cancer of the central nervous system. In a specific example, proliferation of HER2-amplified breast cancer BT-474 cells can be inhibited by bringing the modified antibody-drug conjugate into contact with the cells in vitro. Therefore, it is evident that the inventive method of inhibiting the proliferation of target cells using the modified antibody-drug conjugate as an active ingredient has the effect of killing cells related to the above-described disease or reducing the proliferation rate of the cells.

Hereinafter, the present invention will be described in further detail with reference to examples. It will be obvious to a person having ordinary skill in the art that these examples are not to be construed to limit the scope of the present invention, and various modifications and changes can be made within the technical idea and scope of the present invention.

Unless otherwise defined, the technical or scientific terms as used herein have the same meanings as understood by those having ordinary knowledge in the technical field to which the present invention pertains. Also, detailed description of the same construction and effect as those of the prior art will be omitted herein.

1. ANALYTICAL METHOD 1.1: UV-VIS Spectrophotometry

In the present invention, an antibody-drug conjugate was produced by using a drug (DOX-EMCH) with a linker attached to the anticancer agent doxorubicin (6-maleimidocaproyl)hydrazone. The DOX-EMCH, when injected into a human body, binds to the thiol group of cysteine present in blood albumin to form an albumin-drug conjugate [Willner et al., Bioconjugate Chem. 1993 (4):521-7] and can be easily applied in describing the present invention.

In order to examine whether a drug is still bound to a protein after conjugation and purification steps, UV-VIS absorption spectroscopy is usually employed. Protein shows the maximum absorbance at a wavelength of 280 nm (UV wavelength range), and doxorubicin used in the present invention has the maximum absorbance at 495 nm (visible wavelength range). Both protein and doxorubicin have characteristic absorption coefficients, respectively, at specific wavelength region. Therefore when the absorbance is measured at 280 nm and 495 nm, the equivalent of drug bound per molecule of protein is determined (U.S. Pat. No. 7,528,234 B2).

1.2: In Vitro Cell Proliferation Inhibition Assay

The cytotoxicity or cell proliferation inhibitory activity of the modified antibody-drug conjugate (mADC) was determined by exposing mammalian cells having receptor protein, for example, SK-BR-3 or BT-474 cells, to the modified antibody-drug conjugate (mADC) in cell culture medium. The mADC-treated cells were cultured for about 6 hours ~5 days, and measured its viability.

1.3: Measurement of in vitro Caspase 3/7 Activity

Herceptin does not directly induce cancer cell death, but does induce the death of Her2-positive cancer cells by ADCC (antibody-dependent cellular cytotoxicity). However, a drug therapy directly induces apoptotic cell death, therefore when the caspase activity is measured, it could be determined whether the modified antibody-drug conjugate (mADC) induces caspase-mediated apoptosis or not (Bayascas, et al. (2002), Cell Death and Differentiation. 9: 1078-1089; Preaudat, et al (2002), Journal of Biomolecular Screening. 7: 267-274; Phillips, et al. (2008), Cancer Research 68(22): 9280-9290).

In the present invention, in order to examine the mechanism of apoptosis by the modified antibody-drug conjugate (mADC), the activity of caspase 3/7 was measured. Generally, apoptosis by the modified antibody-drug conjugate (mADC) is determined by exposing mammalian cells having receptor protein, for example, SK-BR-3 cells or BT-474 cells, to the modified antibody-drug conjugate (mADC). The mADC-treated cells were cultured in medium for ~2 days, and was measured its caspase activity.

2. EXAMPLES

Example 1: Preparation of Expression Vector pAV4

Cloning of the expression vector required in the present invention was performed by using a pAV4 vector which was constructed and modified from the parent vector pSGHV0 (GenBank Accession No. AF285183), so as to be used for antibody production in the industrial field. Although human protein could be overexpressed in bacterial cells such as E. coli, it is difficult to obtain as an active substance. Therefore the parent vector was manufactured to express physiologically active protein in high concentration in animal cells in vitro, together with easy purification steps. Albeit its biggest merit of high protein expression level from this parent vector, there is a limitation for its use in the industrial field Therefore the pAV4 vector was modified from its parent vector to be adaptable in the industrial field. In addition, the pAV4 vector is modified adequately for the purpose of expressing both the heavy-chain and light-chain domains of antibody.

Example 2: Construction of Vectors for the Production of Trastuzumab and Cysteine Modified Trastuzumab To construct a trastuzumab (HHL002) vector, the cDNAs of the heavy chain and light chain of trastuzumab were synthesized into codon-optimized sequences so that the expression thereof in CHO cells is maximized. The genes were respectively cloned into the XhoI/NotI and ApaI/SmaI restriction sites of the pAV4 vector, thereby a trastuzumab vector (pHHL002) was prepared.

2.1: Construction of Vectors for the Modified Trastuzumab Antibodies HR-Cys and HR-Cys-Gly-Cys In order to construct vectors for modified trastuzumab antibodies, HR-Cys (HHL002C), a single cysteine mutant in replace of terminal lysine at the C-terminus and another trastuzumab variant HR-Cys-Gly-Cys (HHL002C2) with a C-terminal peptide consisting of Cys-Gly-Cys (CGC), PCR amplification was performed using the constructed trastuzumab vector (pHHL002) as a template. Specifically, PCR amplification was performed using trastuzumab as a template and a XhoHH forward primer (5'-GGG GGG CTC GAG ACC ATG GGT TGG AGC TGT-3') (SEQ ID NO: 116) and an HHNot reverse primer (5'-GCG GCC GGC CGC TCA ACA ACC CGG AGA CAG-3') (SEQ ID NO: 117) for HHL002C or an HHNot reverse primer (5'-GCG GCC GGC CGC TCA ACA GCC ACA ACC CGG AGA CAG-3') (SEQ ID NO: 118) for HHL002C2. The amplified nucleotide sequence was cleaved with the restriction enzymes XhoI and NotI and ligated with the expression vector pHHL002 having XhoI/NotI cleavage sites, thereby constructing cysteine modified trastuzumab antibody vectors (pHHL002C; pHHL002C2). FIG. 1 is a schematic view of the vector. The cysteine-containing variant antibody produced in this Example is a cysteine-containing trastuzumab antibody containing a deletion of lysine at the C-terminus and an addition of single cysteine or a short peptide of cysteine, glycine and cysteine.

2.2: Construction of a Vector for the Modified Trastuzumab Antibody HR-M2(Cys)

In order to construct a vector encoding a modified trastuzumab antibody HR-M2(Cys) (HR-ACHGAACGHA (SEQ ID NO: 119); HHL002M2) which has two metal ion binding motifs (CGH), PCR amplification was performed by using the trastuzumab vector (pHHL002) as a template and a XhoHH forward primer (5'-GGG GGG CTC GAG ACC ATG GGT TGG AGC TGT-3') (SEQ ID NO: 120) and an M2 reverse primer (5' CCCCGC GGC CGC CTA GGC ATG GCC ACA AGC AGC ATG GCC ACA GGC GCC GGG AGA CAG AGA 3') (SEQ ID NO: 121). The amplified nucleotide sequence was cleaved with the restriction enzymes XhoI and NotI and ligated with the expression vector pHHL002 having XhoI/NotI cleavage sites, thereby constructing a cysteine modified trastuzumab antibody vector (pHHL002M2).

2.3: Production of Modified Trastuzumab Antibody HR-M(Cys)

In order to construct a vector encoding modified trastuzumab antibody HR-M(Cys) (HR-GGGACGHA; HHL002M) which has a single metal ion binding motif (CGH), PCR amplification was performed by using an EzChange Site-directed mutagenesis kit (Enzynomics, Ez004S). The above-produced modified trastuzumab antibody HR-M2(Cys) was used as a template with a forward primer (5'-GGT GGA GGT GCT TGT GGC CAT TAA GC) (SEQ ID NO: 122) and a reverse primer (3'-GCC GGG AGA CAG AGA CAG TG) (SEQ ID NO: 123). From the two metal ion binding motifs in HR-M2(Cys), the one metal ion binding motif from the C-terminus was removed and a glycine linker(GGG) was added between the remaining motif and the parent antibody. After EzChange per amplification, the original template HR-M2(Cys) was cleaved with the restriction enzyme DpnI, and the resulting 5-M (Cys) was ligated into a double-stranded DNA vector by ligase, thereby constructing a modified trastuzumab antibody vector (pHHL002M).

2.4: Construction of a Vector for Modified Trastuzumab Antibody HR-M2L(Cys)

In order to construct a vector encoding modified trastuzumab antibody HR-M2L(Cys) (HR-ACGH-AGGGACGHA (SEQ ID NO: 124), HHL002M2L) with an three amino acid linker (GGG) inserted between metal ion binding motifs (CGH), PCR amplification was employed. The above-produced modified vector for trastuzumab antibody HR-M2(Cys) was used as a template with a forward primer (5'-GGT GGA GGTGCT TGT GGC CAT GCC TAA GCG) (SEQ ID NO: 125) and a reverse primer (3'-AGC ATG GCC ACA GGC GCC) (SEQ ID NO: 126). After the original template HR-M2(Cys) was cleaved with the restriction enzyme DpnI, the resulting nucleotide encoding 5-M2L (Cys) was ligated into a double-stranded DNA vector by ligase, thereby constructing a modified trastuzumab antibody vector (pHHL002M2L).

2.5: Construction of a Vector for Modified Trastuzumab Antibody HR-Z(Cys)

In order to construct a vector encoding HR-Z(Cys) (HR-CDICGRKFARSDERKRHTKIHLRQK (SEQ ID NO: 127), HHL002Z) which has a metal ion binding motif from Class I zinc finger protein, PCR amplification was performed using the trastuzumab vector (pHHL002) as a template with a XhoHH forward primer (5'-GGG GGG CTC GAG ACC ATG GGT TGG AGC TGT-3', SEQ ID NO: 1) and a Z reverse primer (5'-GCA TGC GGC CGC CTT ACT TCT GCC GCA GGT GGA TCT TGG TAT GCC TTT TTC GCT CGT CGG ATC TAG CAA ATT TGC GTC CAC AAA TAT CGC ATT TGC CGG GAG ACA GAG A-3') (SEQ ID NO: 128). The amplified nucleotide sequence was cleaved with the restriction enzymes XhoI and NotI and ligated with the expression vector pHHL002 having XhoI/NotI cleavage sites, thereby constructing a cysteine modified trastuzumab antibody (pHHL002Z).

Example 3: Expression and Purification of Trastuzumab and Cysteine Modified Trastuzumab Antibody By using Chinese hamster ovary cells (CHO-K1), the expression of trastuzumab (HHL002) and its cysteine-modified antibodies (HHL002C, HHL002C2, HHL002M, HHL002M2, HHL002M2L, HHL002Z) were analyzed. Specifically, CHO-K1 cells were cultured in DMEM (Dulbecco's Modified Eagle Media) containing 10% FBS (fetal bovine serum) and antibiotic. The CHO-K1 cells were inoculated in a 100 mm culture dish at a concentration of $5 \times 10^6$ cells/ml and then cultured for 24 hour. 800 µl of FBS- and antibiotics-free DMEM was mixed with 10 µg vector and incubated at room temperature for 1 minutes, after which the mixture was mixed with 20 µg PEI (Polyethylenimine, linear, Polysciences Inc (Cat. no: 23966, MW~25, 000)) and allowed to stand at room temperature for about 10-15 minutes. Meanwhile, the cells were washed with PBS and 6 µl of fresh DMEM was added thereto. The trastuzumab or cysteine-modified trastuzumab antibody vector maintained at room temperature for 10-15 minutes was added to the culture dish. On the next day, the cells were washed with PBS, and FBS-free IMDM medium (Cat. No 12200-028, Gibco, Iscove's Modified Dulbecco's Medium) was added thereto to confirm the expression of the antibody protein.

The trastuzumab and cysteine modified trastuzumab antibodies expressed as described above were purified in the following manner. Specifically, in order to purify the trastuzumab and cysteine modified trastuzumab antibodies secreted into the cell culture medium, the culture medium was centrifuged to remove cells, and the supernatant was injected into HiTrap Protein A HP column (GE Healthcare, USA) which was equilibrated with equilibration buffer. The column was sufficiently washed with equilibration buffer and then the protein was eluted by pH change with glycine buffer (100 mM Glycine, pH 2.8). The resulting solution was dialyzed against phosphate buffer, and then concentrated by using Vivaspin20 (Sartorius, USA).

Figure 2:
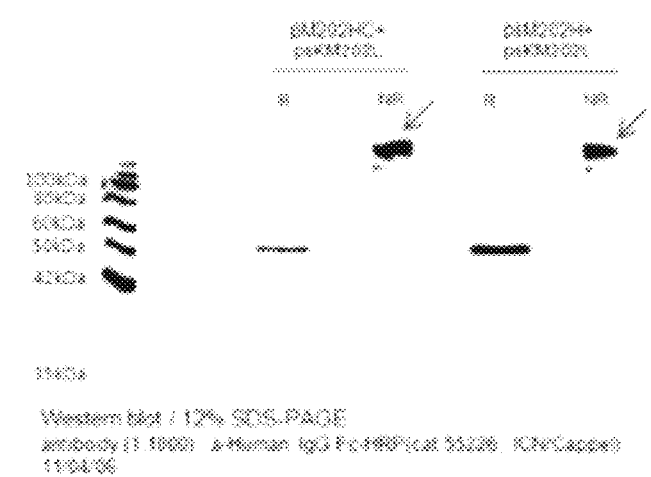
FIG. 2 shows the westernblot image of HR-Cys after purification of trastuzumab (two right lanes) and a cysteine-containing trastuzumab variant (HR-Cys, two left lanes).

Example 4: Production of a Variant Antibody and Drug Conjugate 4.1: Production of a Trastuzumab-Based Variant Antibody and Drug (Doxorubicin) Conjugate In general, if the cysteine residues of proteins do not participate in a intramolecular disulfide bond, the proteins usually form a dimer by intermolecular disulfide bond. However, as shown in FIG. 2, HR-Cys produced in the present invention was present as a whole monomeric antibody as determined by SDS-PAGE and Western blot analysis. In addition, a cysteine residue having a free thiol group in the protein can form a disulfide bond with intracellular glutathione or cysteine. For this reason, in order to break the disulfide bond, a step of treatment with a reducing agent, such as DTT (dithiothreitol) or TCEP (tris(2-carboxyethyl) phosphine), is required upon binding with a drug-second linker, but a sufficient binding reaction can also be achieved even by agitation at room temperature.

The second linker-conjugated drug used in this experiment is a (6-maleimidocaproyl)hydrazone derivative of doxorubicin known as DOXO-EMCH. A method of attaching a compound such as DOXO-EMCH, which has a maleimide group, to the thiol group of protein, is well described in the literature [Klussman, et al. (2004), Bioconjugate Chemistry 15(4): 765-773, page 766; Emmanuel et al. (2010) Chemistry & Biology 2010 (17):213-227].

Figure 3:
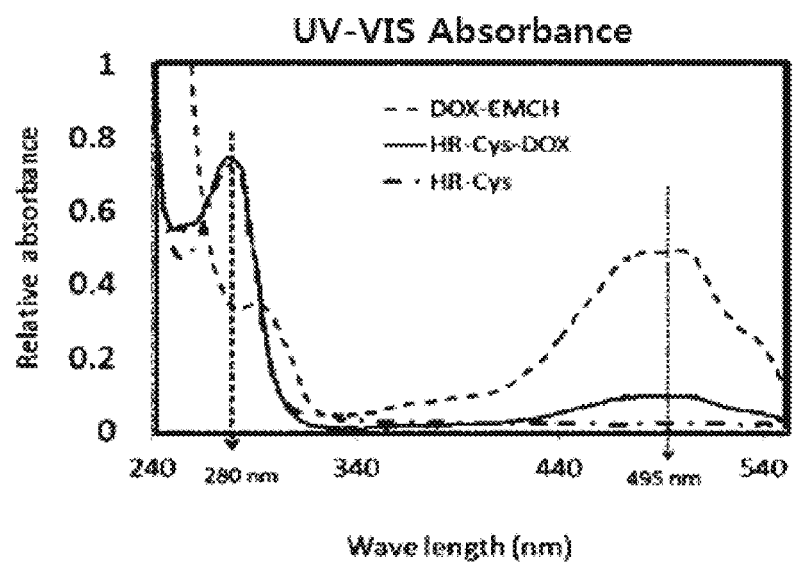
FIG. 3 shows the results of UV-VIS spectrometry (FIG. 3A) and SDS-PAGE (FIG. 3B) performed to confirm whether doxorubicin was conjugated to HR-Cys.
Figure 3:
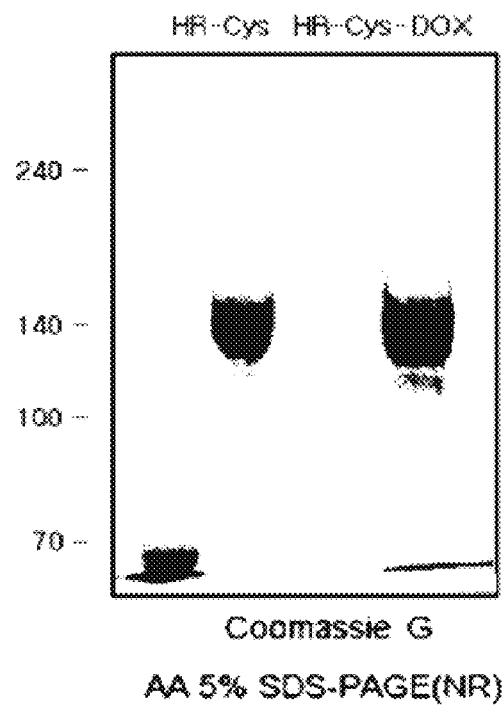

HR-Cys purified in the present invention was mixed with DOXO-EMCH at a molar ratio of 1:10 and agitated at room temperature for 4 hours. Then, the remaining DOXO-EMCH was removed using a desalting column, and the remaining material was washed three times by ultrafiltration, thereby producing a HR-Cys-doxorubicin conjugate (HR-Cys-DOX). The produced conjugate was confirmed by UV-VIS spectrophotometry as shown in FIG. 3. From calculation based on the characteristic absorption coefficients of the protein and the drug, it could be seen that about two molecules of DOXO-EMCH were bound per HR-Cys molecule.

4.2: Production of a Trastuzumab-Based Modified Antibody and Drug (MMAE) Conjugate In the present invention, MMAE known to have cytotoxicity much higher than doxorubicin was conjugated to HR-Cys-GLy-Cys to make a Herceptin-MMAE conjugate (HR-Cys2-MMAE). Monomethyl Auristatin E (see Chemical Formula 2 below), a conjugatable derivative of Auristatin, is linked to the thiol-specific maleimide group through a valine-citurulline, which could be degraded by protease in cells, and a self-degrading spacer, para-aniline benzoic acid (PABA). This is known as MC (maleimido caproic acid)-VC (valine-citurulline)-PAB-MMAE, and a synthesis method thereof is already well known (U.S. Pat. No. 6,214,345; U.S. Pat. No. 7,745,394). Auristatin, a highly cytotoxic compound, is known to have an IC50 value of 200-300 pM in a cell proliferation inhibition assay.

Chemical Formula 2: MC-vc-PAB-Methyl Auristatin E

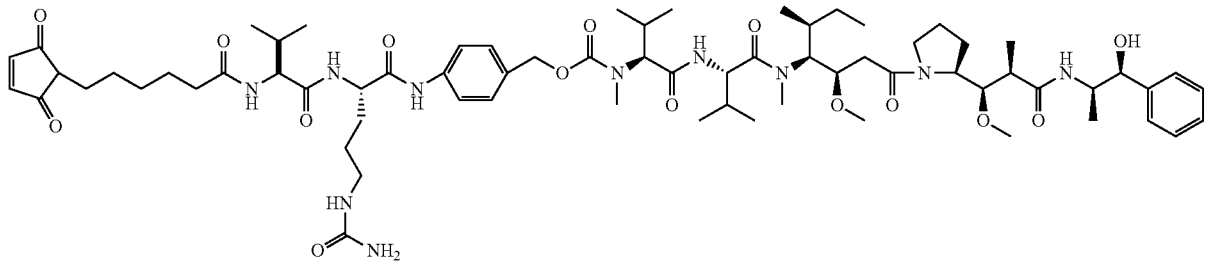 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCC2C(=O)C=CC2=O)C(C)C)cc1)C(C)C]

In the present invention, 2-10 equivalents of the reducing agent TCEP was added to the modified trastuzumab antibody and reacted at 4° C. for 30 minutes to reduce the thiol group, after which 2-10 equivalents of MC-vc-PAB-MMAE was added thereto and reacted at room temperature for about 2-4 hours. The reaction was terminated by addition of an excess amount of cysteine, and unreacted MC-vc-PAB-MMAE and TCEP were removed by centrifugation-filtration and dialysis in phosphate buffered saline, thereby obtaining a purified trastuzumab variant-MC-vc-PAB-MMAE.

In order to confirm the selective binding specificity of the produced trastuzumab variant-MC-vc-PAB-MMAE, the peptide mapping of the produced HR-M2(Cys)-MC-vc-PAB-MMAE was performed (ProteinWorks Co., Ltd., Daejeon, Korea). The results of the peptide mapping indicated that MC-vc-PAB-MMAE was introduced into the peptide cysteine residue that is a drug binding site in the C-terminus of heavy chain. Binding of the drug to the cysteine derived from the intrachain or interchain disulfide bond of the heavy or light chain was not observed. This suggests that the antibody variant designed in the present invention was effectively synthesized, which can significantly increase the homogeneity of the antibody-drug conjugate with the drug bound specifically to the C-terminus of the heavy chain.

4.3: Analysis of Selective Conjugation Property of Modified Trastuzumab Antibody by Using a Maleimide-Containing Fluorescent Dye, Alexa Flour® 488.

In order to examine whether a drug is selectively conjugated to a cysteine residue introduced into the C-terminus of Trastuzumab heavy chain, fluorescent dye Alexa Fluor® 488 substituted with a thiol-specific maleimide group was reacted with each of the modified trastuzumab antibodies. When the cysteine residues of proteins do not form an intramolecular disulfide bond, the proteins usually form a dimer by an intermolecular disulfide bond. However, as shown in FIG. 2, HR-Cys produced in the present invention was present as a whole monomeric antibody as determined by SDS-PAGE and Western blot analysis. In addition, a cysteine residue having a free thiol group can form a disulfide bond with intracellular glutathione or cysteine. For this reason, in order to break the disulfide bond, a step of treatment with a reducing agent, such as DTT (dithiothreitol) or TCEP (tris(2-carboxyethyl)phosphine), is required upon binding with a drug-second linker, but a sufficient binding reaction can also be achieved even by agitation at room temperature. 2-4 equivalents of the reducing agent can reduce not only a cysteine residue introduced into the C-terminus of the heavy chain, but also the intrachain disulfide bond of each of the heavy and light chains and the interchain disulfide bond that links the heavy chain to the light chain. Thus, fluorescent dye can be bound to any cysteine residue reduced by the reducing agent. A drug that is bound to an interchain or intrachain disulfide can reduce the homogeneity of the antibody-drug conjugate, and the bound drug having a relatively large size is highly likely to reduce the structural stability and antigen specificity of the antibody protein itself, and for this reason, the efficacy thereof in the manufacture of biomedicines can be significantly reduced.

2-4 equivalents of TCEP is added to the modified trastuzumab antibody and reacted at 4° C. for about 30 minutes to reduce the thiol group. In this process, either the antibody variant present as a dimer with a disulfide bond or the thiol functional group of cysteine which is present in an oxidant-bound form during an expression process is restored to a reduced form that can bind to a maleimide group. After the reduction reaction, the reducing agent such as DTT, which is reactive to the maleimide group, should be removed by, for example, centrifugation-filtration, but TCEP, which is not involved in the conjugation reaction between the maleimide group and the thiol group, is not necessarily removed. 2-10 equivalents of Alexa Fluor® 488 is added to the modified trastuzumab antibody and reacted with stirring at room temperature for about 2-4 hours. The reaction is terminated by addition of an excess amount of cysteine, and unreacted dye and reducing agent are removed by centrifugation-filtration. The resulting material is dialyzed against phosphate buffered saline, thereby obtaining a modified trastuzumab antibody-Alexa488 dye conjugate.

Figure 4:
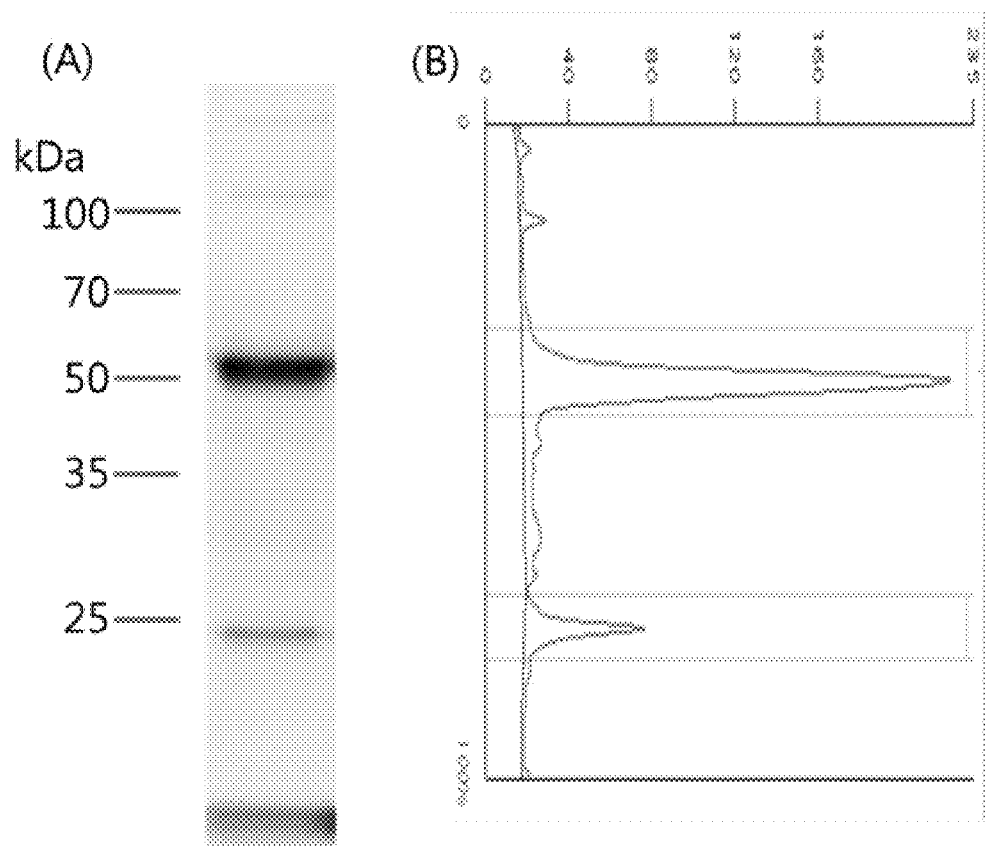
FIG. 4 shows the results of SDS-PAGE gel electrophoresis (FIG. 4A) and the analysis of relative fluorescence intensity of Alexa488 dye bound to each of the heavy and light chains (FIG. 4B) for a Her-M2(Cys)-Alexa488 that is a conjugate of a Her-M2(Cys) antibody variant and Alexa Fluor® 488.

The modified trastuzumab antibody-Alexa488 dye conjugate obtained as described above was separated by SDS-PAGE gel electrophoresis, and then the amount of the dye bound to each of the heavy and light chains was analyzed by a fluorescence image analyzer (Fluorescencen Image Ananlyzer, Typoon9410, Amersharm Bioscience Ltd.). The results of the fluorescence image analysis indicated that, in the case of the HR-Cys and HR-Cys-Gly-Cys antibody variants, the amount of the dye bound to the heavy chain was larger than that of the dye bound to the light chain. Also in the case of HR-M(Cys), HR-M2(Cys), HR-M2L(Cys) and HR-Z(Cys), the amount of the dye bound to the heavy chain was larger than the amount of the dye bound to the light chain. As can be seen in FIG. 4, in the case of the HR-M2 (Cys) antibody variant, the intensity of the fluorescent dye bound to the heavy chain was about 6 times higher than the intensity of the dye bound to the light chain. This difference in fluorescence intensity indicates that the amount of the dye bound to the heavy chain is much larger than the amount of the dye bound to the light chain, suggesting that the selectivity of the maleimide group to the heavy chain is significantly greater.

Example 5: Measurement of Metal Ion Binding Affinity of Metal Ion Binding Motif

As mentioned above, metal ions bind to a peptide having the metal ion binding motif CGH and inhibit or retard the oxidation of the cysteine residue, thereby preventing a sulfonation reaction caused by over-oxidation of the cysteine. Oxidation of the cysteine residue can occur through two reaction pathways. In one reaction pathway, a disulfide bond can be created by thiol-thiol bonding, and in the other pathway, cysteine can also be oxidized by reaction with an excess of oxygen in air to produce sulfenic acid (R—S—OH) as an intermediate product. In this case, the disulfide formation is a reversible reaction in which the disulfide bond can be reduced to thiol, but the formation of sulfenic acid by reaction with oxygen is an irreversible one. When disulfide and sulfenic acid are exposed to oxygen for a long period of time, they are all oxidized to sulfonic acid (R—$SO_3H$) by an irreversible reaction. Because this sulfenic acid or sulfonic acid have no reactivity to maleimide, oxidation to sulfenic or sulfonic acids reduce the reactivity of the antibody variant with maleimide, and thus can greatly influence the conjugation yield and homogeneity of the antibody-drug conjugate.

As described above, it has been reported that a peptide containing the synthetic motif CGH, derived from the metal ion binding motif GGH that is frequently found in vivo, binds metal ions and inhibits the sulfonation of cysteine (Van Horn et al. (2003) J. Biol. Inorg. Chem. 8: 601-610). After secreted to extracellular medium during expression process, antibody protein having the metal ion binding peptide motif can bind to a trace amount of metal ions present in the cell culture medium and effectively inhibits the sulfonation of cysteine. In order to measure the metal ion binding ability of the antibody variant having this metal ion binding peptide motif, the binding affinity was measured by using a Fura-2 (Invitrogen, F-1200), a well-known metal ion chelator. From this measurement, HR-M2(Cys) had a dissociation constant ($K_d$) of about 20 nM, suggesting that it formed a very strong bond with metal ions. In addition, to examine whether the antibody variant having a metal ion binding motif binds to metal ions and protects the cysteine residue, the alkylation rate was measured. It was observed that the antibody variant formed a very strong bond with zinc metal ions, and thus inhibited the cysteine alkylation for up to 24 hours compared to when there was no metal ion. Nickel ions did not bind to the CGH motif as strongly as zinc ions did, suggesting that the effect of inhibiting the cysteine alkylation is lower than that of zinc ions. However, when compared with the buffer without metal ions, nickel ions reduced the alkylation rate of cysteine. When a strong metal ion chelator EDTA was added to remove zinc ions from HR-M2(Cys), it was observed that the alkylation of cysteine occurred quickly, like the case in which there was no extraneously added metal ions.

Figure 5:
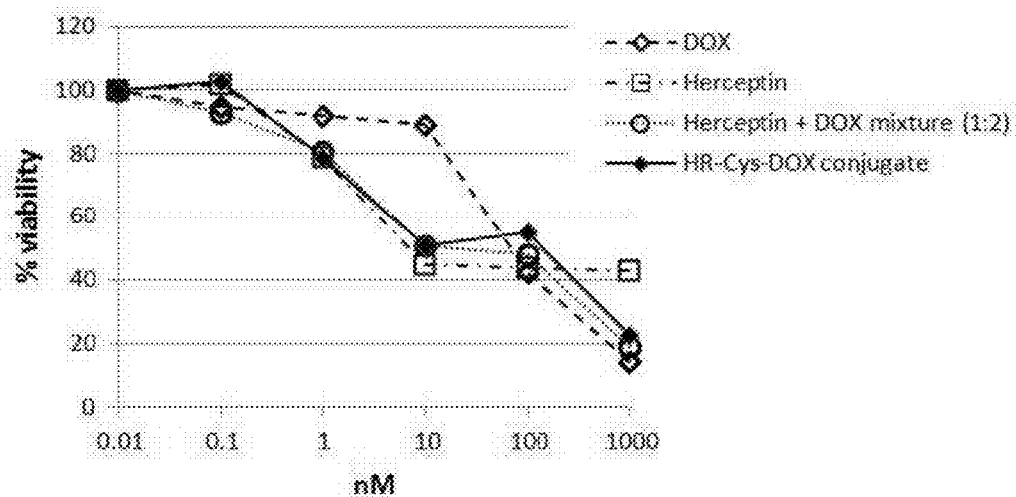
FIG. 5 shows the results of an anti-proliferation MTS assay performed to examine the cell growth inhibitory effect of HR-Cys-DOX in HER2-expressing BT-474 cells in comparison with those of Herceptin, a 1:2 mixture of Herceptin and doxorubicin, and doxorubicin.

Example 6: In Vitro Assay for Cell Proliferation Inhibition 6.1: Cell Proliferation Inhibition Assay of a Variant Antibody and Doxorubicin Conjugate BT-474 cells were diluted with 10% FBS-containing DMEM/F12 medium, and 100 µl of the diluted cell suspension was inoculated into each well of a 96-well plate at a density of $1\times10^4$ cells/well. After inoculation, the well plate was incubated in a 5% $CO_2$ incubator at 37° C. for 24 hours. Each of Herceptin, a 1:2 mixture of Herceptin and doxorubicin, HR-Cys-DOX prepared in the above Example, and doxorubicin, was diluted in medium, and then 100 µl of each dilution was added to each well of the plate at various concentrations of 1000 nM, 100 nM, 10 nM, 1 nM and 0.1 nM. Also medium (having no drug) was added to another wells for negative control. After incubation for about 5 days, 20 µl of CellTiter 96-AQueous One Solution reagent [MTS-based assay; measuring cell proliferation by the amount of purple formazan formed by MTS due to the dehydrogenase of viable cells] was added to each well, followed by incubation in an incubator at 37° C. for 2 hours. 20 µl of 10% SDS solution was added to each well to stop the reaction, followed by sufficient mixing to induce cell lysis. The absorbance of each well was measured by a spectrophotometer, and the viability (%) based on the absorbance is graphically shown in FIG. 5. As a result, it was shown that the cell growth inhibitory effect of HR-Cys-DOX used in low concentrations was similar to those of Herceptin and the 1:2 mixtures of Herceptin and doxorubicin and HR-Cys-DOX at a high concentration showed cytotoxicity similar to that of doxorubicin. These results indicate that HR-Cys-DOX retains the characteristic function of Herceptin and sufficiently exhibits the characteristic cytotoxicity of doxorubicin, even though the doxorubicin is bound Herceptin by the second linker.

Figure 6:
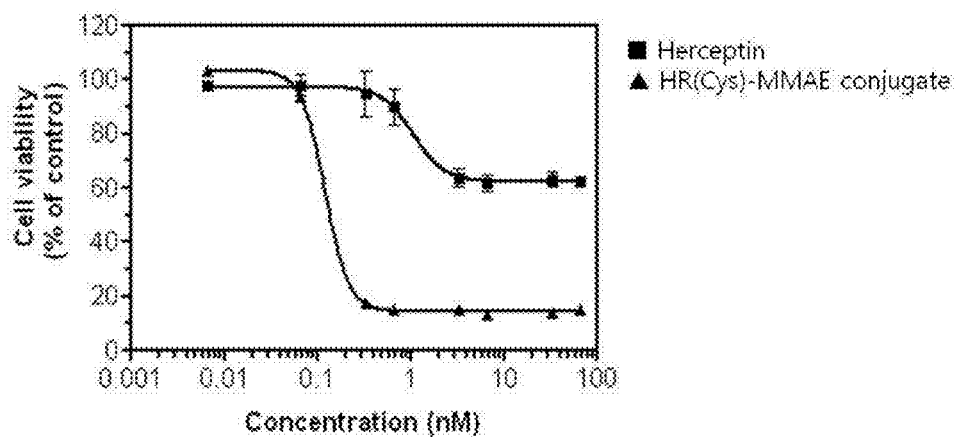
FIG. 6 shows the results of an anti-proliferation assay performed to examine the cell growth inhibitory effect of HER-M(Cys)-MMAE that is a Herceptin-MMAE antibody-drug conjugate in HER2-expressing SK-BR3 cells in comparison with that of Herceptin.

6.2: Cell Proliferation Inhibition Assay of a Variant Antibody and MMAE Conjugate SK-BR3 cells were diluted in 10% FBS-containing DMEM/F12 medium, and 100 µl of the cell diluted suspension was added to each well of a 96-well plate at a density of $1\times10^4$ cells/well. Then, the well plate was incubated in a 5% $CO_2$ incubator at 37° C. for 24 hours. Each of Herceptin and the Herceptin variant antibody-MC-vc-PAB-MMAE conjugate produced in the above Example was diluted in medium, and then added to each well of the plate at various concentrations of 66.7 nM, 33.3 nM, 6.7 nM, 3.3 nM, 0.67 nM, 0.33 nM, 0.067 nM and 0.0067 nM. In addition, medium (having no drug) was added to a control wells for negative control. After incubation for 5 days, 20 µl of CellTiter 96-AQueous One Solution reagent [MTS-based assay; measuring cell proliferation by the amount of purple formazan formed by MTS due to the dehydrogenase of viable cells] was added to each well, followed by incubation in an incubator at 37° C. for 2 hours. The absorbance of each well at 490 nm was measured by a spectrophotometer to determine the cell viability (%). As a result, all of the HR-Cys-MC-vc-PAB-MMAE, HR-Cys-Gly-Cys-MC-vc-PAB-MMAE, HR-M2(Cys)-MC-vc-PAB-MMAE, HR-M(Cys)-MC-vc-PAB-MMAE, HR-M2L(Cys)-MC-vc-PAB-MMAE and HR-Z(Cys)-MC-vc-PAB-MMAE showed excellent cell proliferation inhibitory ability compared to the parent antibody Herceptin. As shown in FIG. 6, the IC50 value of HR-M2(Cys)-MC-vc-PAB-MMAE was at least 5 times lower than that of the parent antibody Herceptin (the median value between the highest and the lowest values was taken for the IC50 for Herceptin because the viability in the case of Herceptin was not lowered to 50% or below). Also, the cell viability at high concentrations was reduced by about 85% for the antibody-drug conjugate, but was reduced only by about 40% for the parent antibody Herceptin. These results indicate that the antibody-drug conjugate has a very high cytotoxicity and a very low IC50 value compared to the parent antibody.

Example 7: In Vitro Assay of Caspase 3/7 Activivation

SK-BR3 cells were diluted with 10% FBS-containing RPMI 1640 medium, and 100 µl of the cell diluted suspension was added to each well of a 96-well plate at a density of $1\times10^4$ cells/well. Then, the 96-well plate was incubated in a 5% $CO_2$ incubator at 37° C. for 24 hours. Each of Herceptin and the modified antibody-drug conjugates produced in the above Example was diluted in medium, and then added to each well of the plate at various concentrations of 66.7 nM, 33.3 nM, 6.7 nM, 3.3 nM, 0.67 nM, 0.33 nM, 0.067 nM and 0.0067 nM. Also medium (having no drug) was added to a control well for negative control. After incubation for 48 hours, 100 µl of Caspase-Glo 3/7 reagent [Caspase-Glo 3/7 assay; measurement of luminescence resulting from the degradation of a caspase substrate by caspase 3/7 activity formed in cells in which apoptosis is induced by the caspase pathway] was added to each well, followed by incubation at room temperature for 30 minutes. Luminescence was measured by a luminometer.

Figure 7:
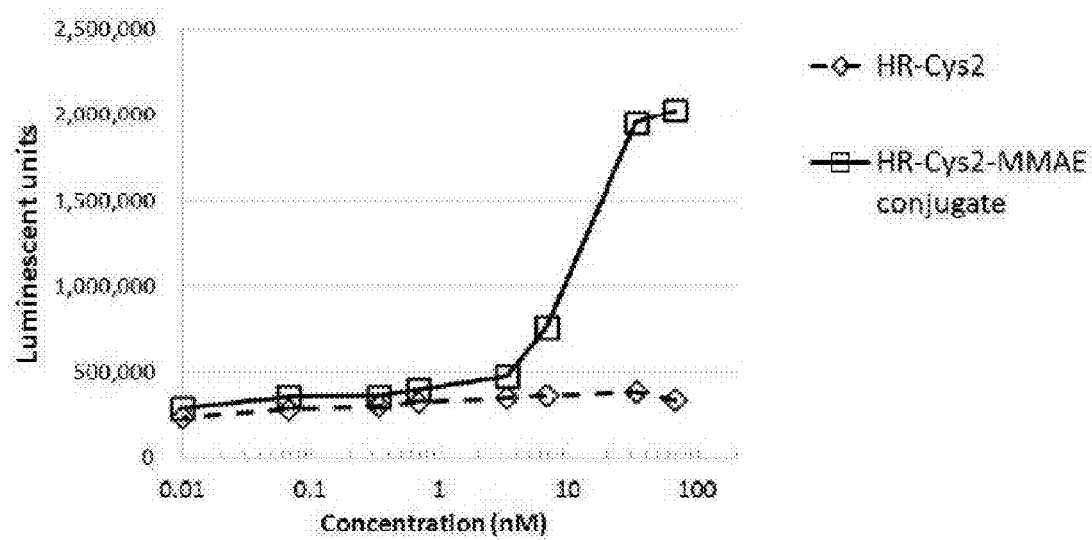
FIG. 7 shows the results of observing caspase activation at various treatment concentrations in order to examine the cell death effect (apoptosis) of HR-Cys2-MMAE in HER2-expressing SK-BR-3 cells in comparison with that of Herceptin.

As shown in FIG. 7, in the cells treated with the parent antibody Herceptin, little or no caspase activity was observed, but in the cells treated with HR-Cys2-MMAE, 3/7 activity increased as the concentration of HR-Cys2-MMAE increased. These results suggest that the MMAE drug released from HR-Cys2-MMAE delivered into the cells induces apoptosis through the caspase pathway, unlike Herceptin.

Figure 8:
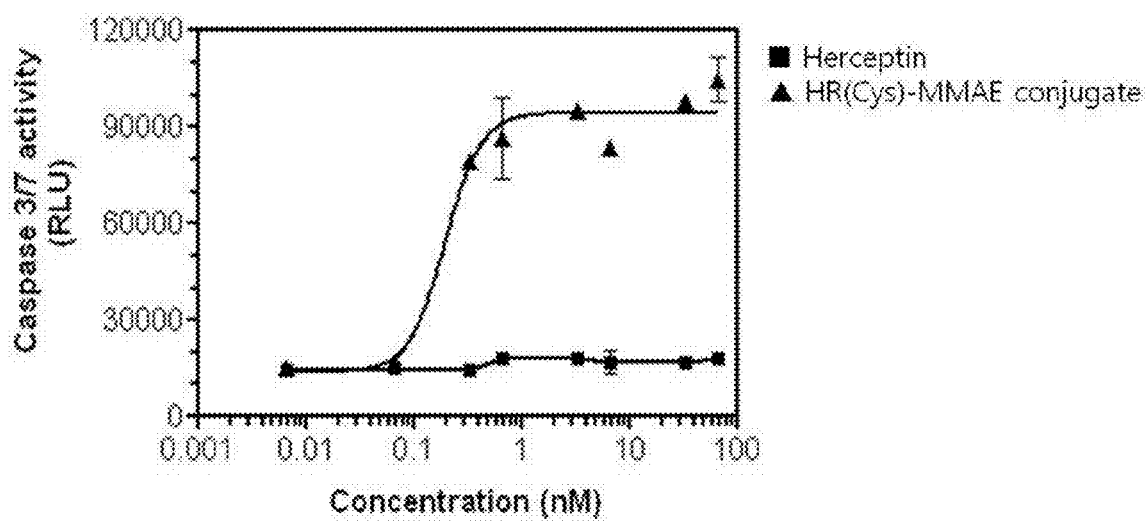
FIG. 8 shows the results of observing caspase activation at various treatment concentrations in order to examine the apoptosis effect of MMAE conjugated to a herceptin antibody variant in HER2-expressing SK-BR3 cells in comparison with that of Herceptin.

In addition, as shown in FIG. 8, in the cells treated with Herceptin, little or no caspase activity appeared, but in the cells treated with HR-M2(Cys)-MC-vc-PAB-MMAE, caspase activity increased as the concentration of HR-M2(Cys)-MC-vc-PAB-MMAE increased. These results indicate that the MMAE drug released from HR-M2(Cys)-MC-vc-PAB-MMAE delivered into the cells induce apoptosis through the caspase pathway, unlike Herceptin.

INDUSTRIAL APPLICABILITY

As described above, the modified antibody of the present invention and the modified antibody-drug conjugate comprising the same can accurately deliver a drug to a target cell due to its high specificity to antigen, and thus can increase the therapeutic effect of the drug. In addition, it can increase the usability of drugs, particularly anticancer agents, the use of which is limited due to their toxicity, despite their high efficacy.

INCORPORATED SEQUENCE LISTING

The specification hereby incorporates by reference the Sequence Listing in the ASCII text file entitled "252SeqID_ST25.txt" created on Nov. 13, 2015 having a size of 37 kB, and filed in the United States Patent and Trademark Office on Nov. 13, 2015.

SEQUENCE LISTING

The Sequence Listing submitted in this application on Aug. 11, 2017 in the 48 kilobyte ASCII text file entitled "252SeqIDListing_ST25.txt" created on the same date of Aug. 11, 2017, including all material in such ASCII text file, is hereby incorporated by reference herein.

The invention claimed is:

1. An antibody-drug conjugate comprising a modified antibody comprising a cysteine-containing motif at the terminus of a parent antibody,
   wherein the cysteine-containing motif is a metal ion binding motif that contains a cysteine residue;
   the metal ion binding motif that contains a cysteine residue is one or two CGH or HGC motif(s) with alanine at C-terminus and N-terminus of the motif, and
   the drug is conjugated to the thiol group of the cysteine residue in the metal ion binding motif.

2. The antibody-drug conjugate of claim 1, wherein the cysteine-containing motif is bound to the terminus of the heavy chain of the parent antibody.

3. The antibody-drug conjugate of claim 2, wherein the cysteine-containing motif is bound to the C-terminus of the heavy chain of the parent antibody.

4. The antibody-drug conjugate of claim 1, wherein the parent antibody is one or more selected from the group consisting of a monoclonal antibody, a bispecific antibody, a chimeric antibody, a human antibody, and a humanized antibody.

5. The antibody-drug conjugate of claim 1, wherein the parent antibody is one or more selected from the group consisting of IgA, IgD, IgE, IgG, and IgM.

6. The antibody-drug conjugate of claim 1, wherein the parent antibody has binding affinity and specificity to cancer-specific antigens, cell surface receptor proteins, cell surface proteins, transmembrane proteins, signaling proteins, cell survival regulators, cell proliferation regulators, molecules associated with tissue development or differentiation, lymphokines, cytokines, molecules involved in cell cycle regulation, molecules involved in vasculogenesis, or molecules associated with angiogenesis.

7. The antibody-drug conjugate of claim 6, wherein the parent antibody comprises one or more selected from the group consisting of trastuzumab, rituximab, bevacizumab, cetuximab, panitumumab, ipilimumab, alemtuzumab, ofatumumab, gemtuzumab, brentuximab, $^{90}$Y-ibritumomab, $^{131}$I-tositumomab, cBR96, cAC10, anti-CD20 antibody, anti-EphB2 antibody, anti-IL-8, E-selectin antibody, anti-MUC16 antibody, anti-CD30 antibody, anti-CD33 antibody, and anti-CD52 antibody.

8. The antibody-drug conjugate of claim 1, wherein the drug is conjugated to the cysteine residue in the motif by a linker, the motif being bound to the parent antibody.

9. The antibody-drug conjugate of claim 8, wherein the linker is one or more selected from the group consisting of alkyl halide derivatives containing a haloacetyl group, derivatives containing a maleimide group, aryl halide derivatives containing fluorobenzene, aziridine derivatives and acryloyl derivatives, wherein the derivatives comprise an alkylating reactive group, an arylating reactive group, a maleimide group, an aziridine group, an acryloyl group, or a disulfide exchange reactive group comprising pyridyl disulfide or thionitrobenzoic acid, which reacts with the thiol group of the cysteine residue in the motif and is covalently bound thereto.

10. The antibody-drug conjugate of claim 1, wherein the drug is one or more selected from the group consisting of microtubulin inhibitors, mitotic inhibitors, topoisomerase inhibitors, chemotherapeutic agents capable of functioning as DNA intercalators, anticancer agents, protein toxins capable of functioning as enzymes, micro-RNA (miRNA), siRNA, and shRNA, which can inhibit the expression of a specific oncogene, and radioisotopes.

11. The antibody-drug conjugate of claim 1, wherein the drug is one or more selected from the group consisting of maytansinoid, auristatin, aminopterin, actinomycin, bleomycin, talisomycin, camptothecin, $N^8$-acetyl spermidine, 1-(2 chloroethyl)-1,2-dimethyl sulfonyl hydrazide, taxol, esperamicin, etoposide, 6-mercaptopurine, dolastatin, trichothecene, CC1065, calicheamicin and other enediyne antibiotics, taxane, anthracycline, methotrexate, adriamycin, vindesine, *vinca* alkaloids, vincristine, vinblastine, etoposide, doxorubicin, melphalan, mitomycin A, mitomycin C, chlorambucil, daunorubicin, daunomycin and stereoisomers, isosteres, or analogs thereof, duocamycin and stereoisomers, isosteres, or analogs thereof, nucleolytic enzymes, antibiotics, toxins of bacterial, plant or animal origin, cisplatin, CPT-11, doxorubicin, paclitaxel, and docetaxel.

12. A method of producing a modified antibody-drug conjugate, comprising:
   (a) reacting a modified antibody comprising a cysteine-containing motif at the terminus of a parent antibody, wherein the cysteine-containing motif is a metal ion binding motif that contains a cysteine residue, and the metal ion binding motif that contains a cysteine residue is one or two CGH or HGC motif(s) with alanine at C-terminus and N-terminus of the motif, with a linker reagent to form an antibody-linker intermediate; and
   (b) reacting the intermediate with an active drug moiety to produce the modified antibody-drug conjugate wherein the drug is conjugated to the thiol group of the cysteine residue in the metal ion binding motif.

13. A method of producing a modified antibody-drug conjugate, comprising:
   (a) reacting a nucleophilic group of a drug moiety with a linker reagent to form a drug-linker intermediate; and
   (b) reacting the intermediate with a parent antibody comprising a cysteine-containing motif at the terminus thereof, wherein the cysteine-containing motif is a metal ion binding motif that contains a cysteine residue, and the metal ion binding motif that contains a cysteine residue is one or two CGH or HGC motif(s) with alanine at C-terminus and N-terminus of the motif, to form the modified antibody-drug conjugate wherein the drug is conjugated to the thiol group of the cysteine residue in the metal ion binding motif.

14. A method of producing a modified antibody comprising a motif bound to a parent antibody, and forming an antibody-drug conjugate therefrom, the method comprising the steps of:
   (a) constructing an expression vector comprising a polynucleotide sequence in which a polynucleotide sequence encoding the motif and a polynucleotide sequence encoding the parent antibody are recombinantly linked to each other;
   (b) expressing the constructed expression vector in a culture using host cells;
   (c) isolating and purifying the modified antibody from the culture; and
   (d) conjugating a drug to the modified antibody to form the antibody-drug conjugate,
   wherein the motif is a cysteine-containing motif at the terminus of the parent antibody, wherein the cysteine-containing motif is a metal ion binding motif that contains a cysteine residue, and the metal ion binding motif that contains a cysteine residue is one or two CGH or HGC motif(s) with alanine at C-terminus and N-terminus of the motif, and
   wherein the drug is conjugated to the thiol group of the cysteine residue in the metal ion binding motif.

15. The method of claim 14, wherein the host cells are selected from the group consisting of monkey kidney cells 7 (COST), NSO cells, SP2/0 cells, Chinese hamster ovary (CHO) cells, W138, baby hamster kidney (BHK) cells, Madin-Darby canine kidney (MDCK) cells, myeloma cell lines, HuT 78 cells, and HEK293 cells.

16. A therapeutic composition comprising the antibody-drug conjugate according to claim 1.

* * * * *

UNITED STATES PATENT AND TRADEMARK OFFICE
CERTIFICATE OF CORRECTION

PATENT NO. : 9,814,782 B2  
APPLICATION NO. : 14/380068  
DATED : November 14, 2017  
INVENTOR(S) : Soon Jae Park Page 1 of 1

It is certified that error appears in the above-identified patent and that said Letters Patent is hereby corrected as shown below:

In the Claims

In Claim 15: "consisting of monkey kidney cells 7 (COST)" should be -- consisting of monkey kidney cells 7 (COS7) --.

Signed and Sealed this  
Second Day of January, 2018

Joseph Matal  
*Performing the Functions and Duties of the*  
*Under Secretary of Commerce for Intellectual Property and*  
*Director of the United States Patent and Trademark Office*